US008835110B2

(12) United States Patent
Wang et al.

(10) Patent No.: US 8,835,110 B2
(45) Date of Patent: Sep. 16, 2014

(54) DNA INTEGRITY ASSAY (DIA) FOR CANCER DIAGNOSTICS, USING CONFOCAL FLUORESCENCE SPECTROSCOPY

(75) Inventors: Tza-Huei Wang, Timonium, MD (US); Kelvin J. Liu, Baltimore, MD (US); Ie-Ming Shih, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 663 days.

(21) Appl. No.: 13/120,060

(22) PCT Filed: Nov. 4, 2009

(86) PCT No.: PCT/US2009/063262
§ 371 (c)(1),
(2), (4) Date: Mar. 21, 2011

(87) PCT Pub. No.: WO2010/053980
PCT Pub. Date: May 14, 2010

(65) Prior Publication Data
US 2011/0171741 A1      Jul. 14, 2011

Related U.S. Application Data

(60) Provisional application No. 61/111,064, filed on Nov. 4, 2008.

(51) Int. Cl.
*C12Q 1/68* (2006.01)
(52) U.S. Cl.
USPC .......................................... 435/6.1; 435/6.14
(58) Field of Classification Search
USPC .................................................. 435/6.1, 6.14
See application file for complete search history.

(56) References Cited

U.S. PATENT DOCUMENTS

2007/0122823 A1    5/2007    Bianchi et al.

OTHER PUBLICATIONS

Sozzi et al., Cancer Research, vol. 61, pp. 4675-4678 (2001).*
Foldes-Papp et al., Experimental and Molecular Pathology, vol. 78, pp. 177-189 (2005).*
Bailey et al. (2009) MS-qFRET: A quantum dot-based method for analysis of DNA methylation, *Genome Res* 19, 1455-1461.
Borgono et al. (2004) Human Tissue Kallikreins: Physiologic Roles and Application in Cancer, *Mol Cancer Res* 2, 257-80.
Boynton et al. (2003) DNA Integrity as a Potential Marker for Stool-based Detection of Colorectal Cancer, *Clin Chem* 49, 1058-1065.
Centonze et al.; 2006. Tutorial on Practical Confocal Microscopy and Use of the Confocal Test Specimen. In Handbook of Biological Confocal Microscopy. J. B. Pawley, editor. Springer, New York. 627-649.
Cesaro-Tadic et al.; 2004. High-sensitivity miniaturized immunoassays for tumor necrosis factor alpha using microfluidic systems. *Lab on a chip* 4:563-569.
Chan et al. (2008) *Clin Cancer Res* 14, 4141-4145.
Chang et al., 2004. Detection of Allelic Imbalance in Ascitic Supernatant by Digital Single Nucleotide Polymorphism Analysis. *Clin Cancer Res* 2580-2585.
Chen, et al. 1999. The photon counting histogram in fluorescence fluctuation spectroscopy. *Biophys. J.* 77:553-567.
Chou et al.; 1999. A microfabricated device for sizing and sorting DNA molecules. *Proceedings of the National Academy of Sciences* 96:11-13.
Diehl et al. (2008) *Nat Med* 14, 985-990.
Dusch et al.; 2007. Three-dimensional point spread function model for line-scanning confocal microscope with high-aperture objective. *J. Microsc.* 228:132-138.
Enderlein et al.; 1997. Statistics of single-molecule detection. *J. Phys. Chem. B* 101:3626-3632.
Enderlein et al.; 1997. The statistics of single molecule detection: An overview. *Bioimaging* 5:88-98.
Enderlein et al.; 1998. Molecular shot noise, burst size distribution, and single-molecule detection in fluid flow: Effects of multiple occupancy. *J. Phys. Chem. A* 102:6089-6094.
Fiegl et al. (2004) *J Clin Oncol* 22, 474-83.
Filippova et al.; 2003. Quantifying double-strand breaks and clustered damages in DNA by single-molecule laser fluorescence sizing. *Biophys. J.* 84:1281-1290.
Foquet et al. (2002) *Anal Chem* 74, 1415-1422.
Foquet et al.; 2004. Focal volume confinement by submicrometer-sized fluidic channels. *Anal. Chem.* 76:1618-1626.
Goodwin et al. 1993. Rapid sizing of individual fluorescently stained DNA fragments by flow cytometry. *Nucl. Acids Res.* 21:803-806.
Goodwin et al.; 1995. Spatial dependence of the optical collection efficiency in flow-cytometry. *Cytometry* 21:133-144.
Habbersett et al.; 2004. An analytical system based on a compact flow cytometer for DNA fragment sizing and single-molecule detection. *Cytometry A* 60:125-134.
Hanley et al. (2006) *Clin Cancer Res* 12, 4569-4574.
Hess et al.; 2002. Focal volume optics and experimental artifacts in confocal fluorescence correlation spectroscopy. *Biophys. J.* 83:2300-2317.
Huang et al.; 2007. Counting low-copy number proteins in a single cell. *Science* 315:81-84.
Huisken et al.; 2004. Optical Sectioning Deep Inside Live Embryos by Selective Plane Illumination Microscopy. *Science* 305:1007-1009.
Jahr et al. (2001) *Cancer Res* 61, 1659-1665).
Liu, Kelvin J. et al., Cylindrical Illumination Confocal Spectroscopy: Rectifying the Limitations of Confocal Single Molecule Spectroscopy Through One-Dimensional Beam Shaping, Biophysical Journal, vol. 95 pp. 2964-2975, Sep. 30, 2008.

(Continued)

*Primary Examiner* — Ardin Marschel
(74) *Attorney, Agent, or Firm* — Venable LLP; Nancy J. Axelrod; Henry J. Daley

(57) ABSTRACT

The present invention relates, e.g., to a method for determining the size distribution of DNA molecules in a sample comprising cell-free nucleic acid, comprising labeling the DNA with a fluorescent dye in a stoichiometric manner, subjecting the DNA to molecular spectroscopy (e.g., cylindrical illumination confocal spectroscopy), analyzing suitable fluorescent burst parameters of the labeled DNA, and conducting single molecule DNA integrity analysis of the labeled DNA molecules in the sample. In one embodiment of the invention, the method is used as a diagnostic method for detecting cancer.

28 Claims, 22 Drawing Sheets

(56) References Cited

OTHER PUBLICATIONS

Motherby et al. (1999) Diagnostic Accuracy of Effusion Cytology, *Cytopathol* 20, 350-357.

Nakayama et al. (2007) Amplicon profies in ovarian serous carcinomas *Int J Cancer* 120 2613-2617.

Parrella et al. (2003) Molecular Analysis of Peritoneal Fluids in ovarian Cancer Patients *Mod Pathol* 16, 636-640.

Piruska et al.; 2005. The autofluorescence of plastic materials and chips measured under laser irradiation. *Lab on a chip* 5:1348-1354.

Qian et al.; 1991. Analysis of confocal laser-microscope optics for 3-D fluorescence correlation spectroscopy. *Appl. Optics* 30:1185-1195.

Rigler et al.; 1993. Fluorescence correlation spectroscopy with high count rate and low-background—analysis of translational diffusion. *Eur. Biophys. J. Biophy.* 22:169-175.

Shih et al. (2007) *Gynecol Oncol* 105 501-507).

Shih et al. "Application of HLA-G Expression in the Diagnosis of Human Cancer" *Hum Immunol.* Apr. 2007: 68(4): 272-276.

Stavis et al.; 2005. Single molecule studies of quantum dot conjugates in a submicrometer fluidic channel. *Lab on a chip* 5:337-343.

Swarup et al. (2007) *FEBS Lett* 581, 795-799.

Tong, Yu-Kwan et al. "Diagnostic developments involving cell-free (cirulating) nucleic acids", Clinica Chimica Acta 363 (2006) 187-196.

Umetani et al. (2006) *J Clin Oncol* 24, 4270-4276.

Umetani, Naoyuki et al., Increased Integrity of Fee Circulating DNA in Sera of Patients with Colorectal or Periampullary Cancer: Direct Quantitative PCR for ALU Repeats, Clinical Chemistry 52:5; pp. 1062-1069, Dec. 30, 2006.

Van Orden et al.; 2000. High-throughput flow cytometric DNA fragment sizing. *Anal. Chem.* 72:37-41.

Wabuyele et al.; 2003. Approaching real-time molecular diagnostics: single-pair fluorescence resonance energy transfer (spFRET) detection for the analysis of low abundant point mutations in K-ras oncogenes. *J. Am. Chem. Soc.* 125:6937-6945.

Wang, Brant G. et al. Increased Plasma DNA Integrity in Cancer Patients, Cancer Res. 2003, 3966-3968.

Xia, Younan et al. Soft Lithography Angew. Chem. Int. Ed. 1998, 37 550-575.

Yan, Xiaomei et al. Chracteristics of Different Nucleic Acid Staining Dyes for DNA Fragment Sizing by Flow Cytometry, Anal. Chem. 1999, 71, 5470-5480.

Yeh, Hsin-Chih et al. Homogeneous point mutation detection by quantum dot-mediated two-color fluoresence coincidence analysis, *Neuceic Acids Research*, 2006, vol. 34, No. 5.

Yokokawa, Ryuji et al. Transcriptome analysis device based on liquidphase detection by fluorescently labeled nucleic acid probes, Biomed Microdevices (2007) 9:869-875.

Zhang, Chun-Yang et al. Single-quantrum-dot-based DNA nanosensor, nature materials. vol. 4, Nov. 2005 www.natuer.com/naturematerials.

Umetani, Naoyuki et al., "Increased Integrity of Fee Circulating DNA in Sera of Patients with Colorectal or Periampullary Cancer: Direct Quantitative PCR for ALU Repeats", Clinical Chemistry 52:5; pp. 1062-1069, Dec. 30, 2006.

Liu, Kelvin J. et al., "Cylindrical Illumination Confocal Spectroscopy: Rectifying the Limitations of Confocal Single Molecule Spectroscopy Through One-Dimensional Beam Shaping", Biophysical Journal, vol. 95 pp. 2964-2975, Sep. 30, 2008.

\* cited by examiner

DNA INTEGRITY ASSAY (DIA) FOR CANCER DIAGNOSTICS, USING CONFOCAL FLUORESCENCE SPECTROSCOPY

This application is a National Stage Application of International Application No. PCT/US2009/063262 filed Nov. 4, 2009, which claims priority to U.S. Provisional Application No. 61/111,064 filed Nov. 4, 2008, the entire contents of both of which are incorporated by reference in their entirety. Co-pending U.S. application Ser. No. 12/612,300, filed on Nov. 4, 2009, contains related information and is incorporated by reference herein in its entirety.

This application was made with U.S. government support, including grants number 0546012, 0730503, and 0725528 from The National Science Foundation. The U.S. government thus has certain rights in the invention.

FIELD OF THE INVENTION

This invention relates, e.g., to a method for detecting nucleic acid integrity in cell-free nucleic acid, using single molecule spectroscopy methods and/or systems. In one embodiment of the invention, cylindrical illumination confocal spectroscopy (CICS) systems and methods are employed. This method can be used, e.g., as a diagnostic method for detecting cancer.

BACKGROUND INFORMATION

Cell-free nucleic acids (CNAs) consist of extra-cellular genetic material freely found in human body fluids, including circulating body fluids. These information rich molecules are an excellent source of non-invasive biomarkers as they are readily released into the body from both pathologic and healthy cells. They are being extensively studied in a diverse array of human diseases such as cancer, fetal medicine, and diabetes (Swamp et al. (2007) *FEBS Lett* 581, 795-799; Tong et al. (2006) *Clin Chim Acta* 363, 187-196). In cancer, CNAs can be used to determine the status of remote tumors through the analysis of both genetic and epigenetic information, potentially bypassing the need for tissue biopsies. They have been demonstrated throughout cancer management in the assessment of tumor dynamics, therapeutic response, disease progression, and prognosis (Diehl et al. (2008) *Nat Med* 14, 985-990; Umetani et al. (2006) *J Clin Oncol* 24, 4270-4276; Wang et al. (2003) *Cancer Res* 63, 3966-3968).

Despite the potential benefits, the clinical analysis of CNA biomarkers faces two key hurdles. First, CNAs are present at very low concentrations within the body (~10-400 ng/mL in plasma) and, second, CNAs of interest must be accurately discerned from a sea of obscuring background CNAs. To date, PCR-based methods have been used near exclusively due to its high sensitivity. While PCR has been very successful in biomarker discovery and research, it has intrinsic limitations. For example, PCR is a complicated enzymatic process that requires substantial optimization to obtain favorable results, making PCR finicky and somewhat difficult to reliably reproduce on a daily basis. More complicated variants, such as quantitative real-time PCR (qPCR) and nested PCR, require yet more care, making robust quantification and multiplex detection difficult. qPCR has wide dynamic range but is typically limited to measuring 2-fold changes in quantity. Multiplexed PCR reactions can also be affected by varying amplification efficiencies, leading to poor quantification accuracy. Furthermore, the sensitive nature of the PCR process and the lack of standardization in sample preparation steps can further exacerbate these issues. Practically, long run times, tedious sample processing steps, expensive reagents, and trained technicians required for PCR, limit its clinical utility.

One way of analyzing CNAs to detect cancer is the DNA Integrity Assay (DIA). This is a unique cancer biomarker that is highly specific to cancer in general, but not to cancer type. Rather than relying on sequence or epigenetic information contained within the CNAs, DIA uses the size distribution of CNA fragments to determine their origin. Apoptotic cells are postulated to release uniform pieces of 180 bp long DNA while tumor cells, which tend to die haphazardly through necrosis and cell lysis, release fragments of much longer and more variable length (Jahr et al. (2001) *Cancer Res* 61, 1659-1665). The apoptotic origins of typical short DNA strands have recently been verified by sequencing studies. DIA may have high utility in early detection and screening of cancer, particularly for cancers in which no widely accepted markers currently exist. It was first demonstrated for the detection of colon and gynecological cancers (Wang et al. (2003) *Cancer Res* 63, 3966-3968; Boynton et al. (2003) *Clin Chem* 49, 1058-1065) and subsequently for the detection of breast, nasopharyngeal, and prostate cancer (Umetani et al. (2006) *J Clin Oncol* 24, 4270-4276; Chan et al. (2008) *Clin Cancer Res* 14, 4141-4145; Hanley et al. (2006) *Clin Cancer Res* 12, 4569-4574). The size distribution of these cell-free DNAs may be used as a marker for cancer detection and potentially to monitor therapeutic efficacy and disease recurrence (Umetani et al. (2006, supra); Chan et al. (2008, supra).

There is a need to develop methods that can be used instead of, or in addition to, PCR to analyze CNAs and, in particular, to conduct DNA Integrity Assays (DIA).

DESCRIPTION OF THE DRAWINGS

FIG. 2A: DNA sizing histograms were taken as the laser power was adjusted from 0.6 mW to 3.7 mW. A steeper dependence of burst size on DNA size was seen at higher laser powers leading to higher DNA sizing resolution (inset). FIG. 2B: Smaller DNA fragments within the mixture reach optical saturation at lower laser powers than larger DNA fragments due to the decreased number of fluorophores contained within. c) DNA sizing histograms were taken at 3 different fluidic drive pressures. Slower flow velocities lead to higher resolution due to the steeper slope between burst size and DNA size and decreased Poisson variability.

3A as a function of DNA threshold value. This marker has the greatest distinguishing power when the threshold is set at ~800 bp, at which the stage IV patient has an smDIA value nearly 7× that of the stage I patient.

Figure 4:
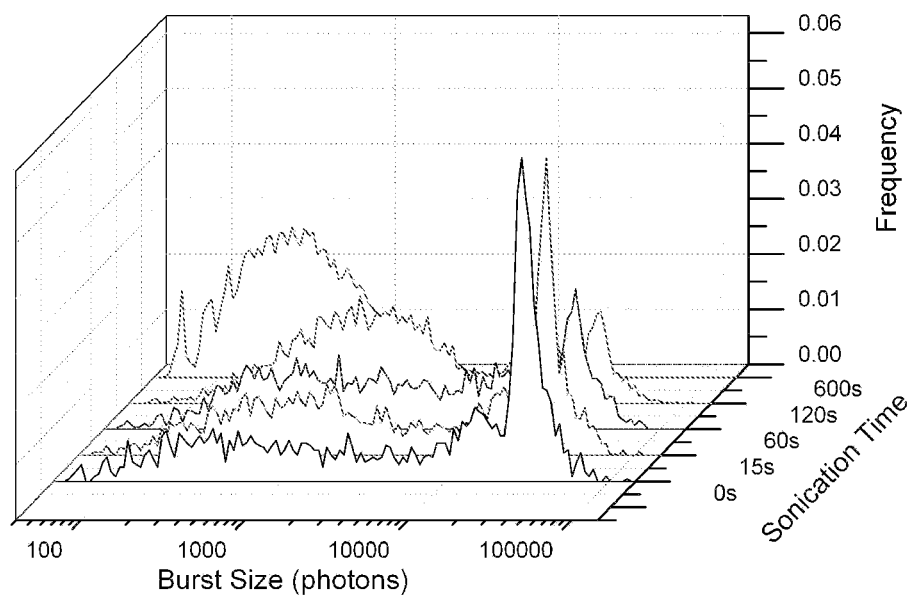

FIG. 4 shows DNA sizing histograms of ultrasonically sheared λ DNA taken using μCICS.

Figure 5:

FIG. 5 shows a gel electrophoresis image of ultrasonically sheared λ DNA. Lane 1—Hind III Ladder, Lane 2—0 s, Lane 3—15 s, Lane 4—60 s, Lane 5—120 s, Lane 6—600 s.

Figure 6:
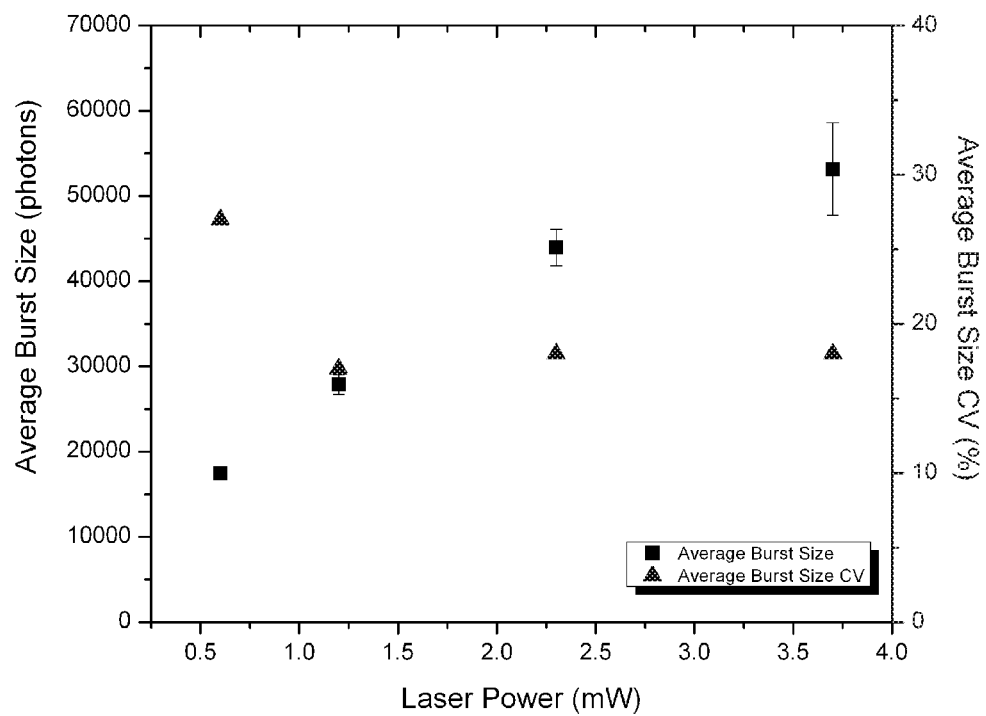

FIG. 6 shows laser power effects on average burst size and measurement CV. The average burst size increases with laser power but shows optical saturation effects as the increase deviates from linear (squares). The measurement CV stays constant between 1.2-3.7 mW of laser excitation power but increases at 0.6 mW of power due to increased Poisson variability and lower S/N ratio.

Figure 7:
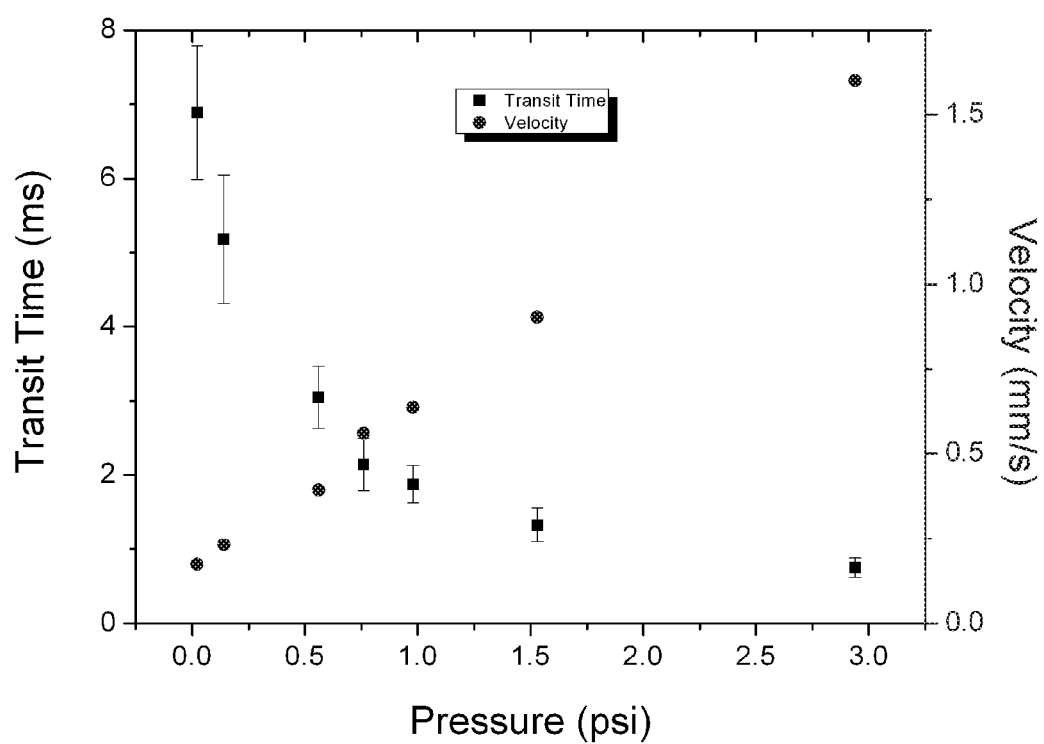

FIG. 7 shows pressure—velocity measurements using fluorescent tracer beads. The tracer beads can be used to measure molecular transit time as a function of pressure (squares). The transit time can then be used to calculate flow velocity. The flow velocity exhibits the expected linear relation to pressure (circles).

Figure 8:
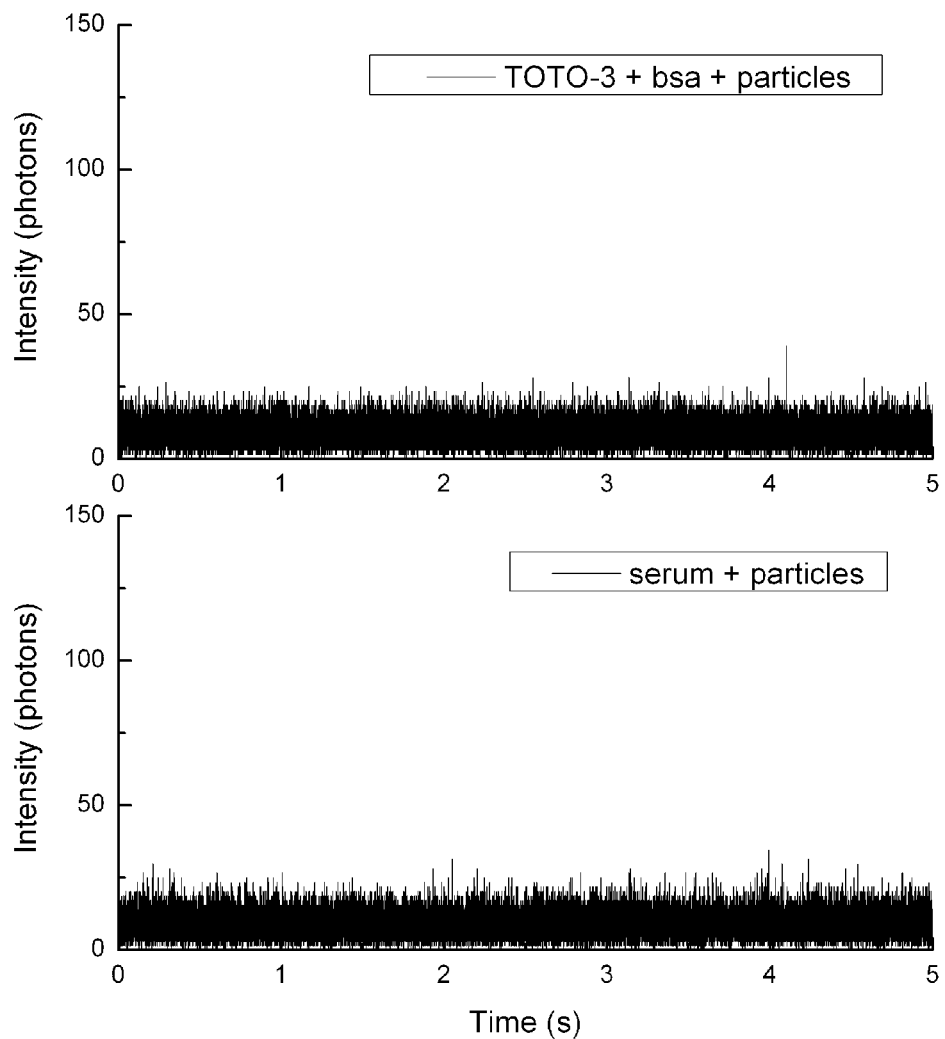

FIG. 8 shows μCICS data taken of controls samples with TOTO-3, 7.5% BSA solution and 0.04 μm fluorescent tracer particles (top panel) or serum and 0.04 μm fluorescent tracer particles (bottom panel). Both samples contain extremely few background bursts due to non-specific staining (top) or sample auto-fluorescence (bottom). The samples were tested using the same protocol as the clinical samples.

Figures 9A, 9B, 9C, 9D:
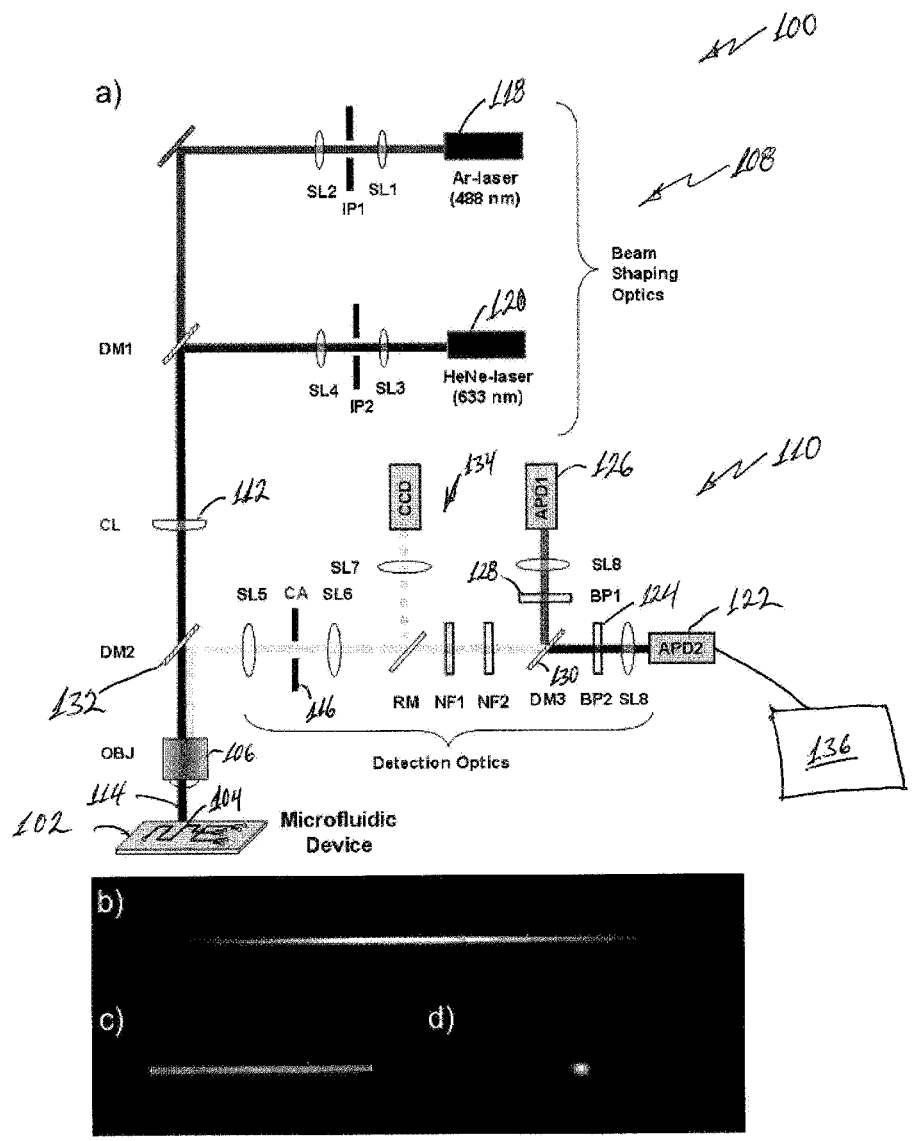

FIG. 9A is a schematic illustration a cylindrical illumination confocal spectroscopy (CICS) system according to an embodiment of the current invention. FIG. 9B shows reflected images of the illumination volume of the system of FIG. 9A, but with no aperture. FIG. 9C corresponds to FIG. 9B, but a 620×115 μm rectangular aperture was included. FIG. 9D is the case of conventional SMD with no pinhole. The conventional SMD illumination volume resembles a football that extends in and out of the plane of the page while the CICS observation volume resembles an elongated sheet or plane that also extends in and out of the page. The CICS observation volume is expanded in 1-D using a cylindrical lens (CL) and then filtered using a rectangular aperture (CA). In the absence of a confocal aperture in FIG. 9B, the CICS illumination profile is roughly Gaussian in shape along the x, y, and z axis, chosen to align with the width, length, and height of a microchannel, respectively. The addition of the confocal aperture in FIG. 9C, depicted as a rectangular outline, allows collection of fluorescence from only the uniform center section of the illumination volume. Abbreviations: SL—spherical lens, IP—illumination pinhole, CL—cylindrical lens, OBJ—objective, DM—dichroic minor, CA—confocal aperture, BP—bandpass filter, RM—removable minor, NF—notch filter, CCD—CCD camera, APD—avalanche photodiode FIG. 10A-10F show the illumination, I (top), collection efficiency, CEF (middle), and observation volume, OV (bottom), profiles of traditional SMD (left) and CICS (right) calculated using a semi-geometric optics model. The profiles are illustrated as xz-plots. Traditional SMD has a small OV profile that varies sharply in the x- and z-directions while the CICS OV profile has a smooth plateau region that varies minimally. The units of illumination profile and OV profile are arbitrary units (AU).

Figures 11A, 11B:
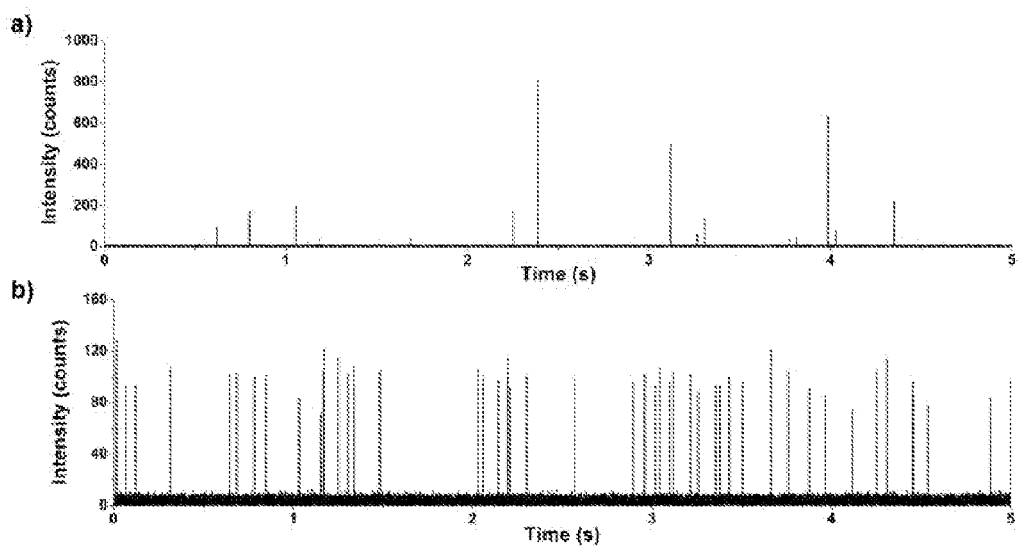

FIGS. 11A and 11B show simulated single molecule trace data of FIG. 11A standard SMD and FIG. 11B CICS performed using Monte Carlo simulations and the theoretical OV profiles. CICS displays a significant increase in burst rate and burst height uniformity over traditional SMD. An increase in background noise is also evident. The bin time was 0.1 ms.

Figures 12A, 12B:
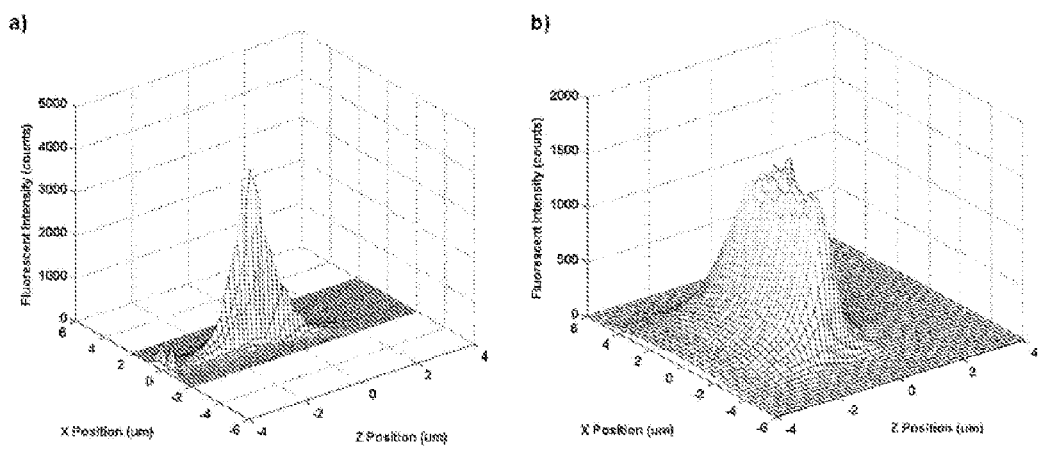

FIGS. 12A and 12B show OV profiles of FIG. 12A traditional SMD and FIG. 12B CICS acquired using a sub-micron fluorescent bead. The CICS observation volume resembles traditional SMD in the z-direction but is elongated in the x-direction such that it can span a typical microchannel.

FIGS. 13A-13F show Gaussian curve fits of the OV profiles shown in FIG. 12 for standard 488-SMD (left) and 488-CICS (right). The CICS profiles are similar to the standard SMD profiles in the y- and z-directions but appear substantially elongated in the x-direction. Good fits are obtained for all except CICS in the x-direction which is not expected to be Gaussian. A slightly better approximation of the curve shape can be obtained if a Lorentzian fit is used in the z-direction rather than a Gaussian fit. (Gaussian Fit: y=y0+(A/(w*sqrt(PI/2)))*exp(-2*((x-xc)/w)^2).

Figures 13A, 13B, 13C, 13D, 13E, 13F:
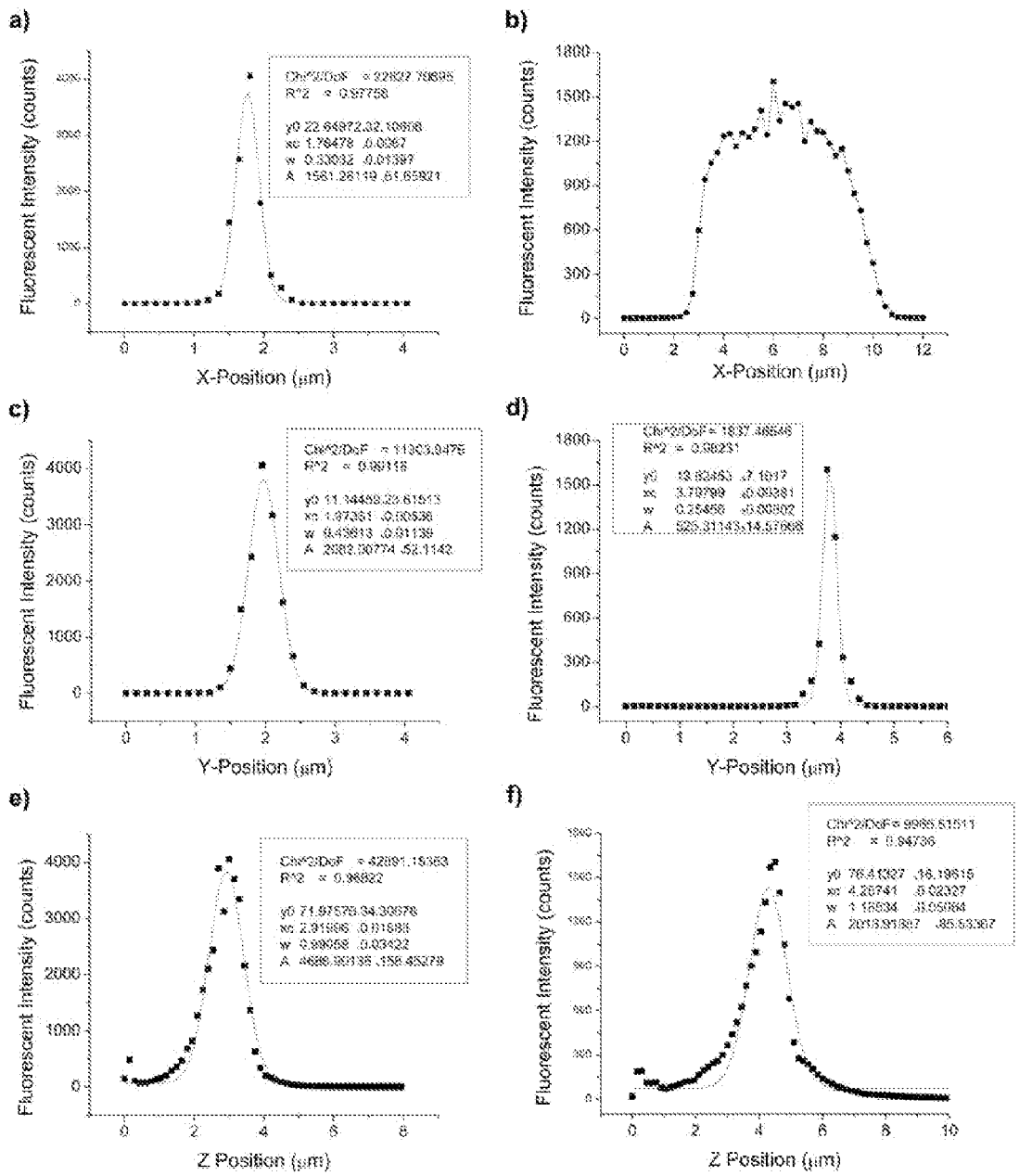
Figure 14:
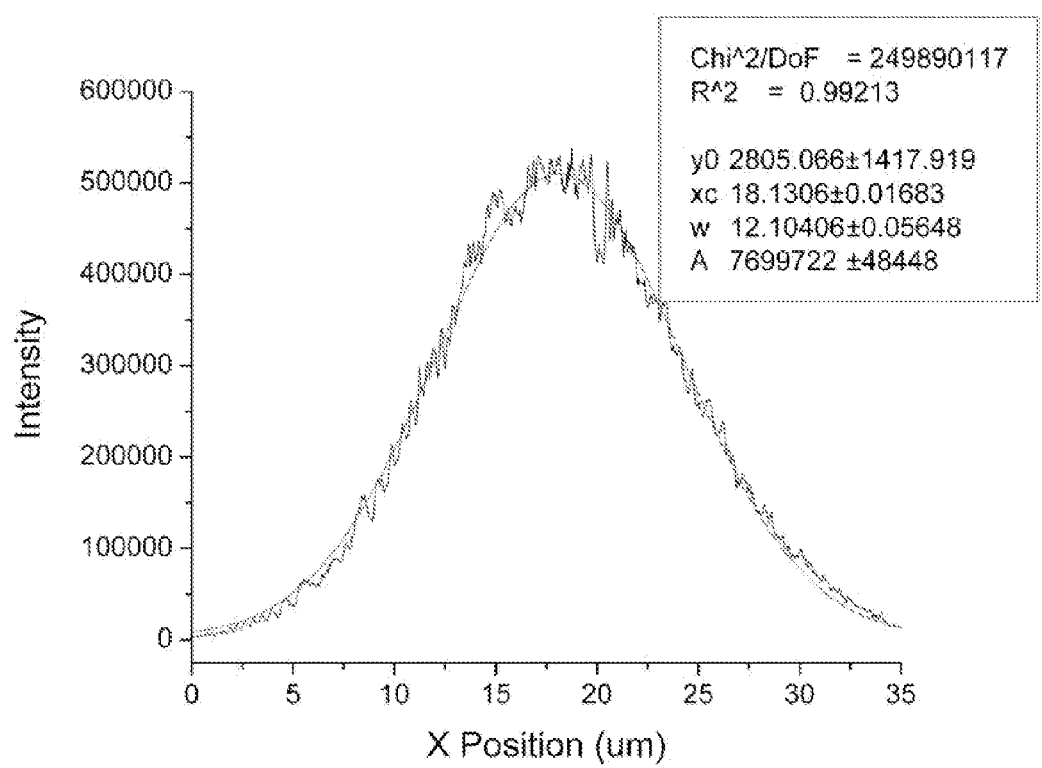

FIG. 14 shows image analysis of the 488-CICS illumination volume depicted in FIG. 13D before the confocal aperture. The sum of each column of pixels within the illumination volume is plotted as a function of the x-position. Before filtering with the aperture, the illumination follows a Gaussian profile with a $1/e^2$ radius of 12.1 μm. (Gaussian Fit: y=y0+(A/(w*sqrt(PI/2)))*exp(-2*((x-xc)/w)^2).

Figure 15:
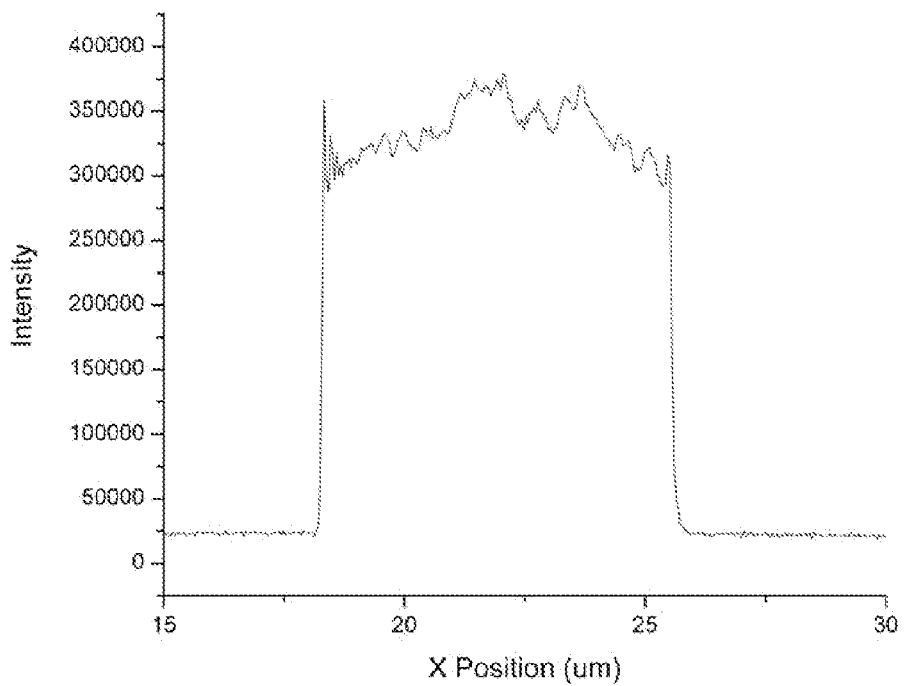

FIG. 15 shows image analysis of 488-CICS illumination volume depicted FIG. 13C after the confocal aperture. The sum of each column of pixels within the observation volume is plotted as a function of the x-position. After filtering with the aperture, light is collected from only the uniform center 7 μm.

Figure 16:
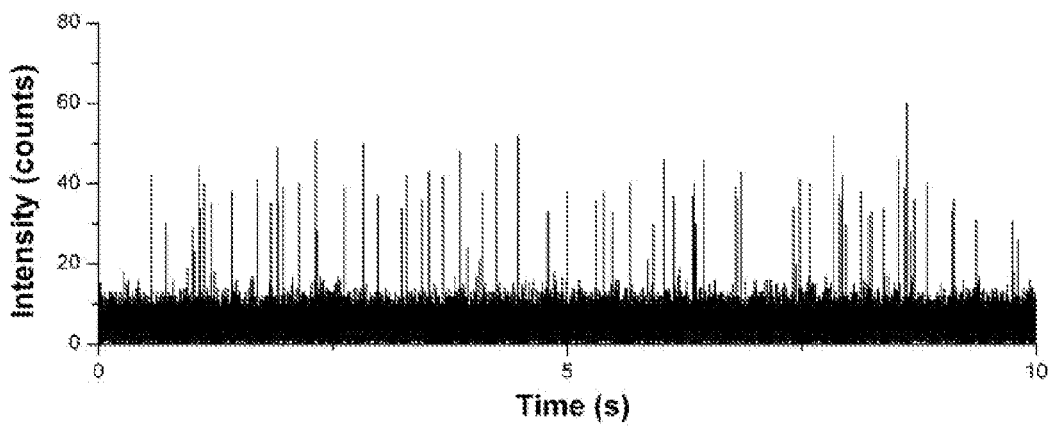

FIG. 16 shows single molecule trace data of PicoGreen stained pBR322 DNA taken using 488-CICS. The fluorescence bursts appear at a high rate and are highly uniform, but the background appears elevated due to the high amounts of background scatter from the silicon substrate. The bin time was 0.1 ms and 0.08 mW/cm2 of illumination power was used.

Figure 17:
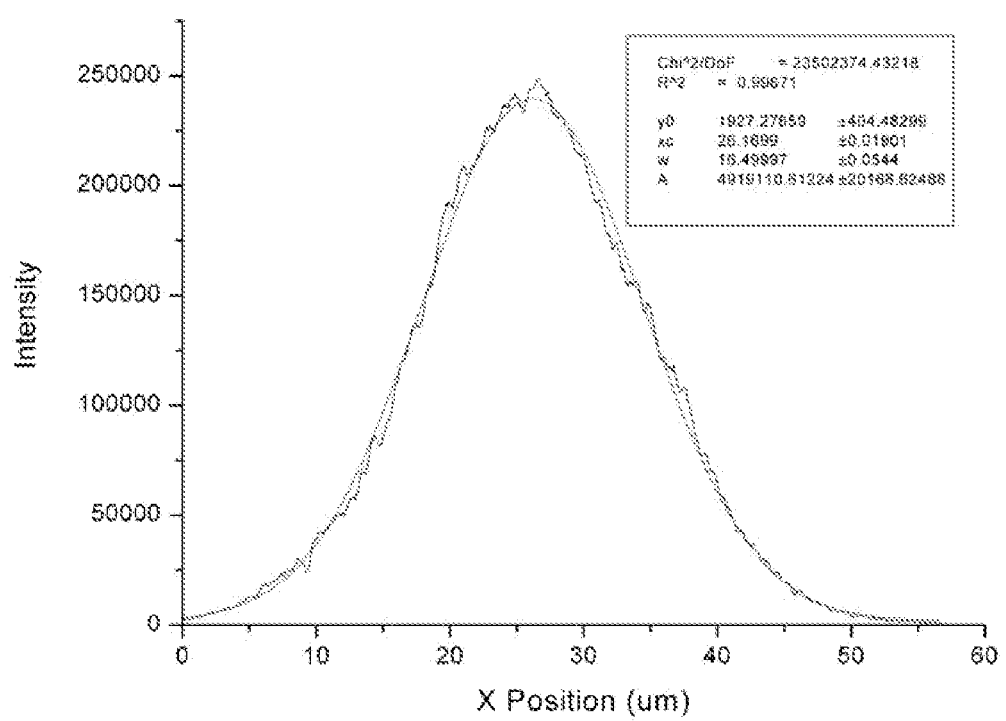

FIG. 17 shows image analysis of 633-QCS. The sum of each column of pixels within the illumination volume is plotted as a function of the x-position. Before filtering with the aperture, the illumination follows a Gaussian profile with a $1/e^2$ radius of 16.5 μm. This radius is approximately 30-fold greater than the $1/e^2$ radius of the diffraction limited 633-SMD illumination volume. (Gaussian Fit: y=y0+(A/(w*sqrt(PI/2)))*exp(-2*((x-xc)/w)^2).

Figure 18:
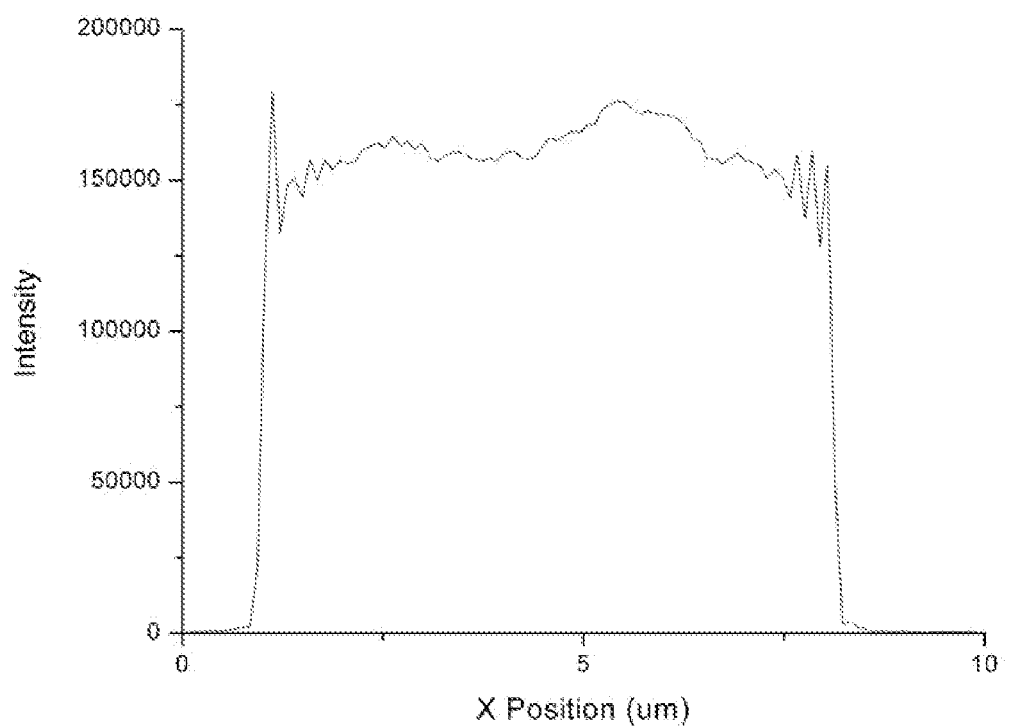

FIG. 18 shows image analysis 633-QCS. The sum of each column of pixels within the observation volume is plotted as a function of the x-position. After filtering with the aperture, light is collected from only the uniform center 7 μm.

Figure 19:
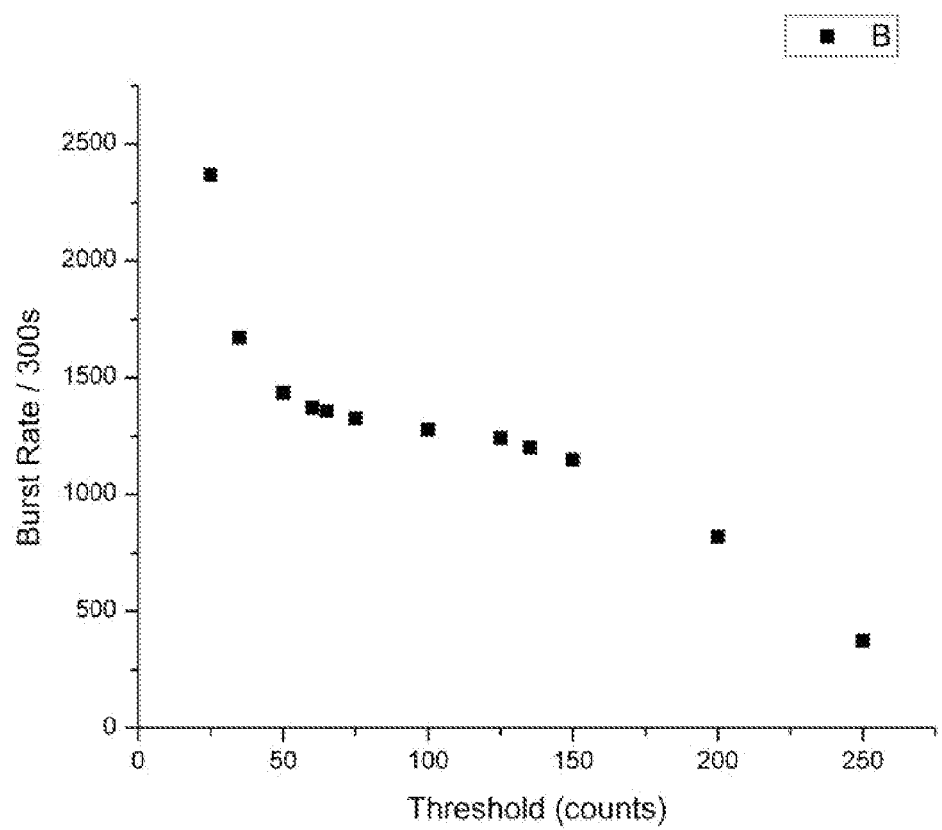

FIG. 19 shows threshold effects on burst rate in 633-CICS analysis of TOTO-3 in a 5×2 μm PDMS microchannel. CICS data is much less sensitive to thresholding artifacts. There is a flat region between thresh=65-125 where the burst rate remains fairly constant. The illumination power was 1.85 mW/cm$^2$, and the bin time was 0.1 ms.

Figure 20:
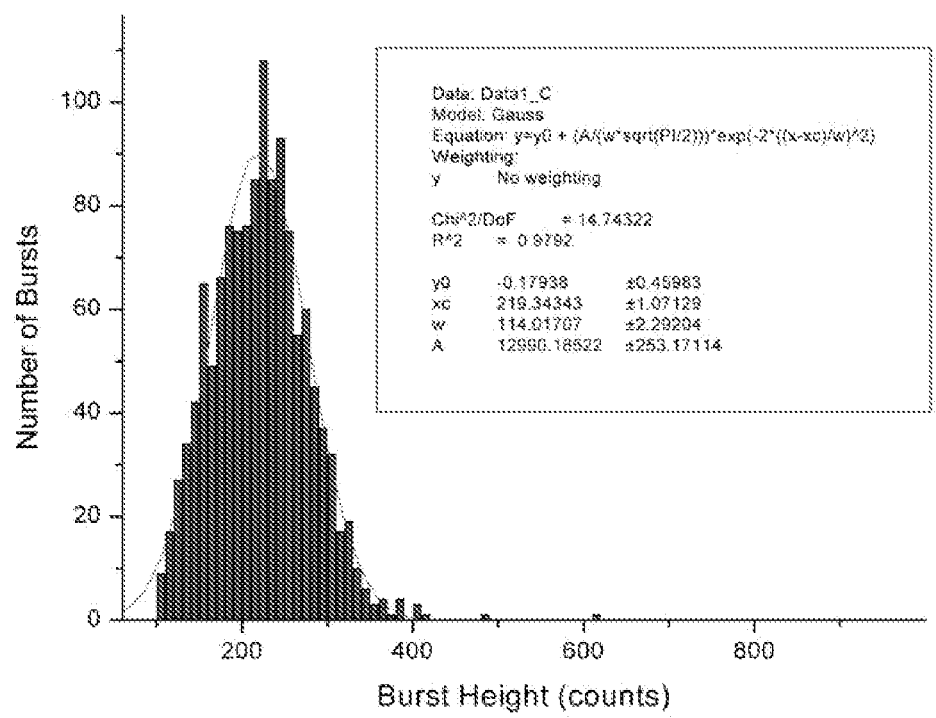

FIG. 20 is a burst height histogram of the CICS data presented in FIG. 17. The burst height histogram shows a sharp, well-defined Gaussian peak centered at 219 counts. Also depicted is a Gaussian curve-fit.

Figure 21:
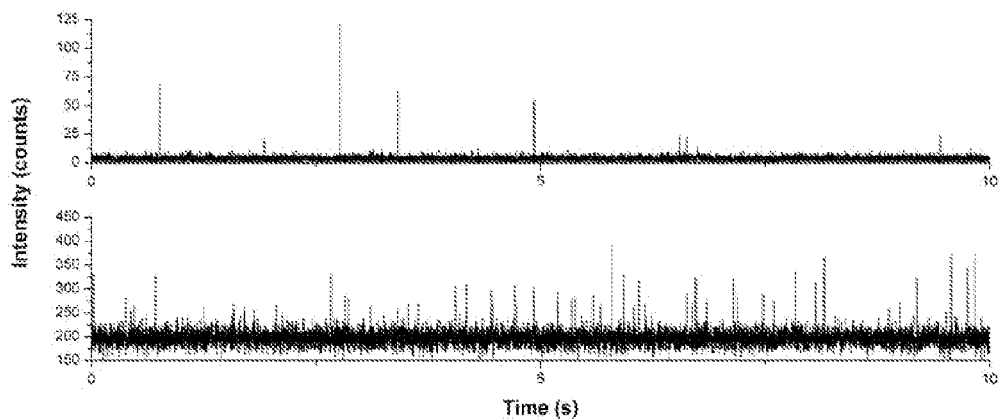

FIG. 21 is single molecule trace data of Cy5 labeled oligonucleotides taken using 633-SMD (top) and 633-CICS (bottom). Cy5 bursts can be clearly discriminated even above the high background. The background appears higher than the TOTO-3/pBR322 traces in FIG. 9 because of the longer bin time and higher excitation power. The bin time was 1 ms while 0.185 mW/cm$^2$ and 3.7 mW/cm$^2$ of illumination power was used for SMD and QCS, respectively.

Figure 22:
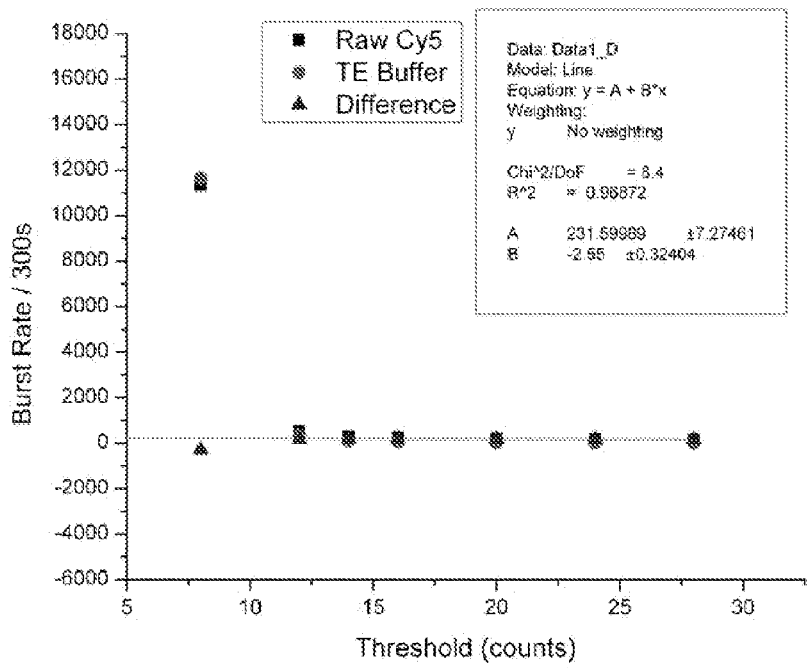

FIG. 22 shows threshold effects on burst rate in 633-SMD analysis of Cy5 in a 5×2 μm PDMS microchannel. As the threshold is increased, the burst rate first increases slowly and then increases sharply as the number of false negative bursts rises sharply. A linear fit is applied to the points at t=16, 20, 24 and 28 and used to extrapolate the number of detected bursts if the threshold was set to 0. The illumination power was 0.185 mW/cm$^2$, and a 1 ms bin time was used.

Figure 23:
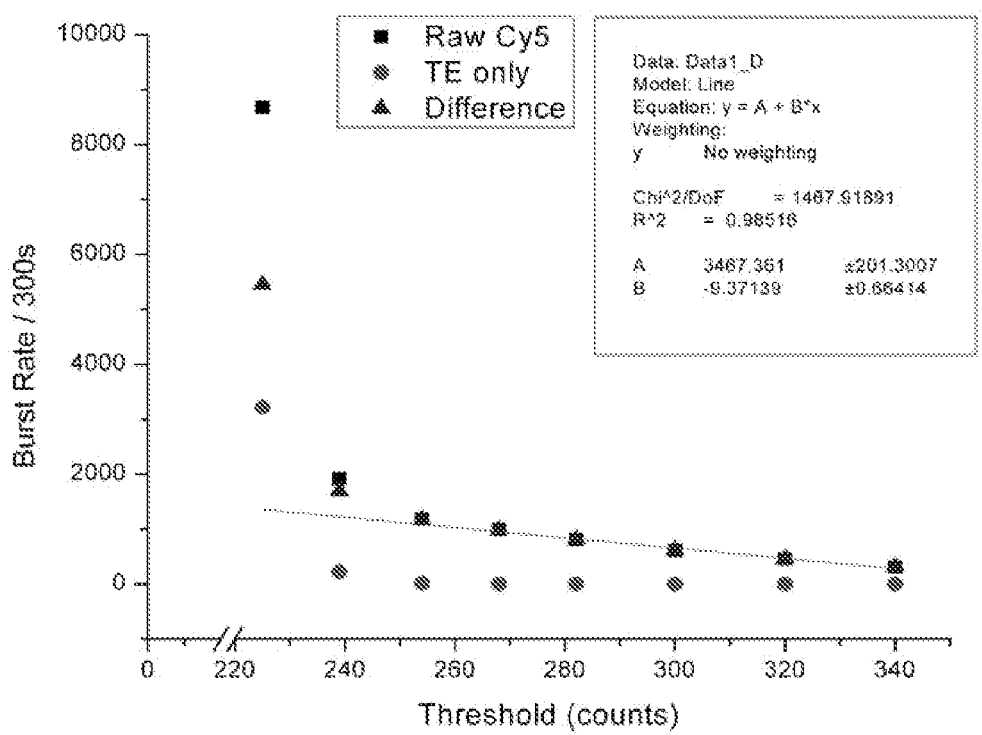

FIG. 23 shows threshold effects on burst rate in 633-CICS analysis of Cy5 in a 5×2 μm PDMS microchannel. A linear fit is applied to the points at t=268, 282, 300, 320, and 340 and used to extrapolate the number of detected bursts if the threshold was set to 0. The illumination power was 3.7 mW/cm$^2$, and the bin time was 1 ms.

Figure 24:
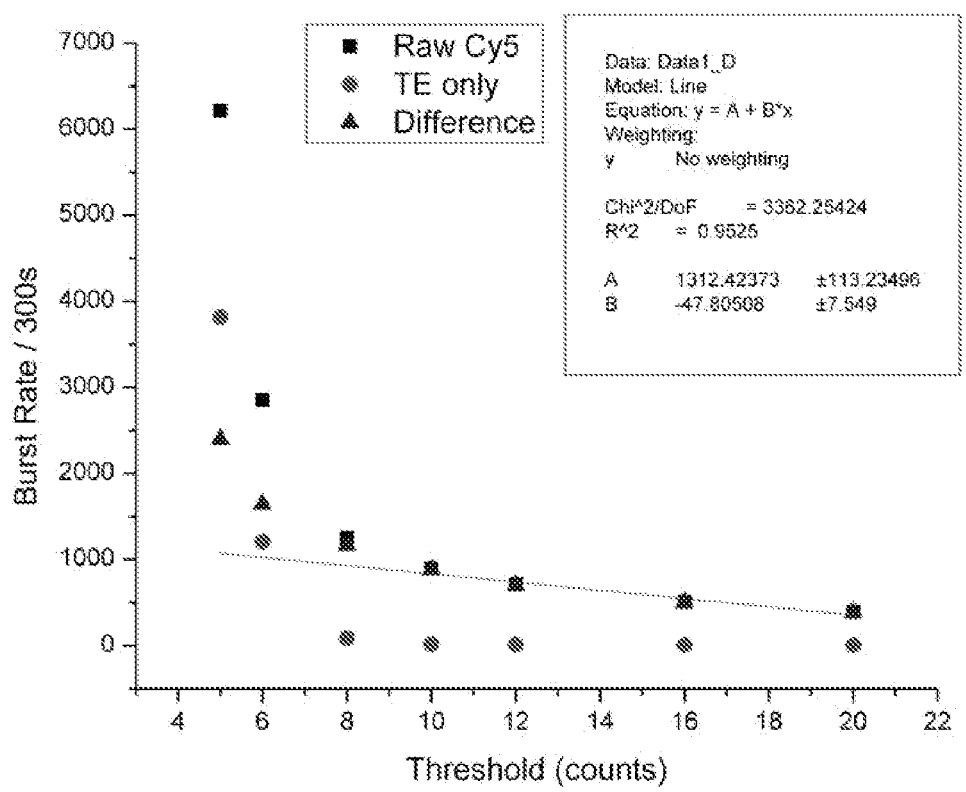

FIG. 24 shows threshold effects on burst rate in 633-SMD analysis of Cy5 in a 100 μm ID silica microcapillary. A linear fit is applied to the points at t=10, 12, 16 and 20 and used to extrapolate the number of detected bursts if the threshold was set to 0.1312 molecules were detected while 3×10$^6$ molecules are expected based on the 1 μl/min flow rate, 1 pM concentration, and 300 s data acquisition time. This leads to a mass detection efficiency of 0.04%. The illumination power was 0.185 mW/cm$^2$, and the bin time was 1 ms.

Figure 25:
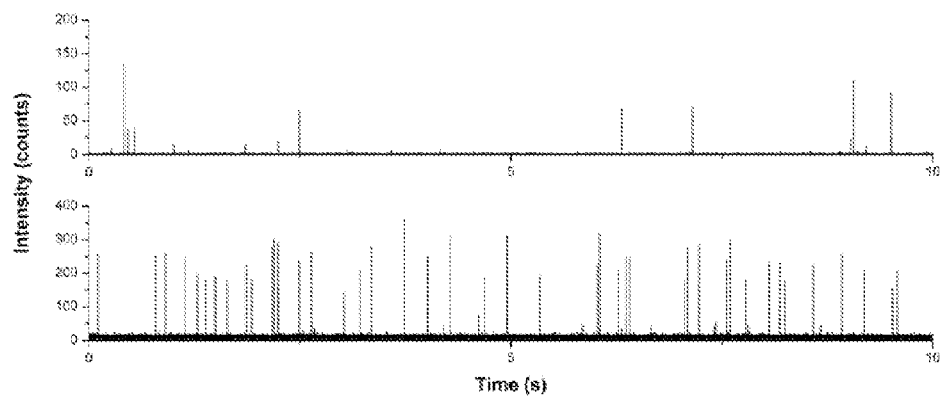

FIG. 25 shows experimental single molecule trace data of TOTO-3 stained pBR322 DNA taken using SMD (top) and CICS (bottom). The CICS experimental data shows a high burst rate and burst height uniformity that parallels the results of the Monte Carlo simulations. The bin time was 0.1 ms.

Figure 26:
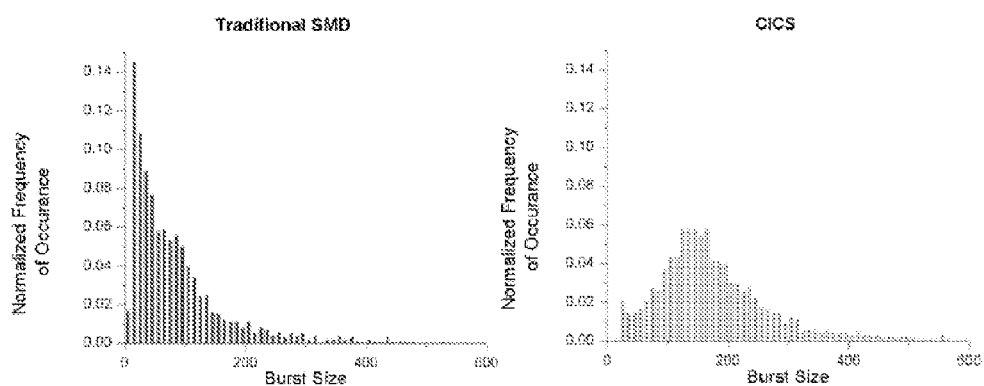

FIG. 26 shows BSDA histograms of PicoGreen stained pBR322 DNA taken using standard SMD (left) and CICS (right). In standard SMD, the DNA peak is not resolved from the noise fluctuations due to the Gaussian OV profile whereas CICS shows a clearly discernable peak due to the high uniformity of the OV profile.

DESCRIPTION

The present inventors have developed methods for detecting cancer, comprising conducting DNA Integrity Assay (DIA) analysis of cell-free nucleic acids (CNAs), using methods of single molecule spectroscopy. Methods of single molecule spectroscopy that can be used in a method of the invention employ, e.g., nanochannel-based DNA sizing, flow cytometry-based DNA sizing, or cylindrical illumination confocal spectroscopy (CICS) (e.g., microfluidic cylindrical illumination confocal spectroscopy (μCICS)).

In particular, the inventors report the development of a single molecule assay for CNA analysis based on microfluidic cylindrical illumination confocal spectroscopy (μCICS), which can be used for the clinical analysis of DNA size and quantity. μCICS uses a 1-D focal volume expansion and matched microfluidic constriction to achieve high detection uniformity, 100% mass detection efficiency, and higher throughput than conventional diffraction-limited CS-systems. One feature of this embodiment of the method is that it insures a substantially uniform detection profile. This assay can be performed directly on patient serum without DNA isolation or separation and uses only a single reagent, making it well suited for clinical diagnostic applications.

Furthermore, the high sensitivity of CICS enables the direct elucidation of the DNA fragment size distribution without the need for enzymatic amplification (e.g., PCR). Confocal spectroscopy (CS) can be used to analyze rare biomolecules. CS can be used in conjunction with DNA nanosensors to detect molecules from 5 fM-0.5 nM in concentration, a range that overlaps well with the physiological serum concentrations of CNAs, which range from 5-200 ng/ml, corresponding to nanomolar levels of CNAs (Zhang et al. (2005) *Nat Mater* 4, 826-831).

In a method of the invention, the CICS platform is used in the measurement of fluorescent burst size to determine the size and distribution of the cell-free DNA molecules. DNA molecules in a CNA sample of interest are labeled in a stoichiometric manner with a fluorescent dye, such that the amount of label is proportional to the length of the DNA molecules, and fluorescence burst parameters are measured which indicate the length of each of the DNA molecules. Fluorescent burst parameters that can be used to measure the length of the DNA include, e.g., burst size, burst height and transit time. Burst size, the integrated or total number photons emitted by a single molecule within a fluorescent burst, is linearly related to DNA length across a wide dynamic range of sizes. Burst height, the maximum number of photons emitted by a single molecule within a single acquisition period of a fluorescent burst, and transit time, the time it takes a molecule to traverse the focal volume, are also linearly related to DNA length but for a more narrow range of DNA sizes where DNA conformation does not change dramatically. In addition, the fluorescent burst rate indicates the abundance of DNA molecules of each size that are measured. Burst rate refers to the rate at which the individual bursts are detected (i.e. the number of fluorescent bursts detected in a given period of time). By controlling and calibrating for flow velocity, laser power, focus position, etc., one can readily determine the size of each DNA molecule independently, without being misled, for example, by superimposed DNA molecules. In essence, the length of each of the DNA molecules in a sample, and the number of molecules of each size, are determined. This size distribution can then be quantitatively used, e.g. in the clinical management of cancer.

For illustrative purposes, in the Examples herein the data are analyzed by fluorescent burst size analysis (BSDA), which is a method for visualizing the data in the form of a histogram. For more practical purposes, for the analysis of clinical samples, the data are analyzed by calculating a single molecule DNA integrity index (smDI), which quantifies the ratio of large to small DNA molecules (long DNA bursts to short DNA bursts) in the sample. This smDI can be analyzed as an absolute value, or it can be compared to negative and/or positive reference standards, as is described in more detail below.

In the Examples herein, the inventors first demonstrate that μCICS can be used to accurately size DNA from 564 bp-23.1 kbp. Critical operation parameters such as flow rate, laser power, and constriction size are explored and shown to have predictable effects on DNA sizing performance. Then, the assay is used to analyze serum samples from early and late stage lung cancer patients. This assay serves as an illustrative example as to the potential of microfluidic single molecule spectroscopy and complementary fluorescent probes/nanosensors as a rapid, facile, and efficient alternative to traditional PCR based methods for CNA analysis.

Embodiments of the invention have a number of advantages. For example, cell-free DNA samples for analysis in certain embodiments of the inventive method can be obtained readily and relatively non-invasively, e.g. from urine, stool, blood samples, or other suitable body fluids, which avoids the unpleasantness and side-effects of invasive procedures (such as tissue biopsies) and is especially useful for the detection of a cancer in an inaccessible tissue. DIA detects neoplasms in general, and is not limited to the detection of particular types of cancer. Thus, a method of the invention can be used for routine cancer screening and treatment monitoring.

Other advantages of a method of the invention include that it is rapid, economical, simple, robust, highly sensitive, specific and accurate. With regard to the embodiment of the invention using CICS, advantages include that the method uses only a single reagent, a single labeling step, and can be performed directly from patient serum without the need for DNA isolation. The one-step staining protocol is afforded by dye choice and assay design. By designing the assay such that all DNA within the sample is saturated with dye molecules and selecting a dye that has only a single, high-affinity binding mode, the labeling reaction becomes insensitive to exact staining ratio. The absence of the need to adjust the staining ratio eliminates the need to predetermine DNA concentration and thus simplifies the assay. Additionally, the high detection efficiency ensures that only minute amounts of sample are required (<10 pL). A method of the invention can detect cancers at an earlier stage than can conventional cytology methods; for example, one can detect cancers which are at the curable stage (stage 1 or stage 2). A method of the invention avoids additional pitfalls of using rt-PCR analysis, as discussed above.

One aspect of the invention is a method for determining the size distribution of DNA molecules in a sample comprising cell-free nucleic acids, comprising labeling the (individual) DNA molecules in the sample with a fluorescent dye in a stoichiometric manner, subjecting the labeled DNA to single molecule spectroscopy, and analyzing fluorescent burst parameters of the labeled DNA, wherein the fluorescent parameters, burst size, burst height and/or transit time, indicate the length of each of the DNA molecules; and the fluorescent burst rate indicates the abundance of each size of DNA molecule, and conducting single molecule DNA integrity analysis (smDIA) of the labeled DNA molecules in the sample.

The single molecule spectroscopy may be carried out using flow cytometry or using nanochannels, or it may be cylindrical illumination confocal spectroscopy (CICS), e.g., microfluidic cylindrical illumination confocal spectroscopy (μCICS).

In one embodiment of this method, the single molecule spectroscopy is conducted by causing the sample comprising the labeled DNA molecules to flow through a channel of a fluidic device, illuminating a portion of the fluid flowing through the channel substantially uniformly with a sheet-like beam of light that activates the fluorescent dye, directing fluorescing light from the labeled DNA molecules to be detected through a substantially rectangular aperture of an aperture stop to be detected, wherein the substantially rectangular aperture is constructed and arranged to substantially match a width of said channel, and detecting the labeled DNA molecules based on light directed through the substantially rectangular aperture.

In a method of the invention, the calculation of the smDIA may comprise correlating substantially quantized light pulses with the lengths of the DNA molecules detected (the length of a DNA molecule correlates with the size of the burst), and calculating the single molecule DNA integrity (smDI) (the number ratio of long DNA bursts detected over the number of short DNA bursts) of DNA molecules in the sample. The distinction between long and short DNA bursts may be defined by a predetermined cut-off value or range of values. The sample may be a body fluid (e.g., a cell-free body fluid).

The method may further comprise comparing the smDI to a positive and/or a negative reference standard.

One aspect of the invention is a method as above, for determining if a subject is likely to have a cancer, wherein an absolute value of smDI is used to determine if the subject is likely to have the cancer. In this method, the sample is a body fluid (e.g. a cell-free body fluid) from the subject; the single molecule spectroscopy is CICS or μCICS; and the smDIA comprises correlating substantially quantized light pulses with the lengths of the DNA molecules detected, and calculating the single molecule DNA integrity (smDI) of DNA molecules in the sample. The smDI is compared to a predetermined cut-off value. An smDI of at least about 0.04, 0.06, 0.08, 0.10, 0.125, 0.15, 0.175, 0.2, 0.3, 0.4, 0.5, 0.6, 0.7 0.8, or 0.9 indicates that the subject is likely to have the cancer.

Another aspect of the invention is a method as above, for determining the tumor load in a subject, wherein the smDI is compared to a positive and/or a negative reference standard. In this method, the sample is a body fluid from the subject; the single molecule spectroscopy is CICS or μCICS; and the smDIA comprises correlating substantially quantized light pulses with the lengths of the DNA molecules detected, and calculating the single molecule DNA integrity (smDI) of DNA molecules in the sample. The method further comprises comparing the smDI of the DNA molecules in the sample to a positive and/or a negative reference standard, wherein the negative and positive reference standards are representative of defined amounts of tumor load.

Such a method may be used to determine if a subject is likely to have a cancer. In this embodiment, the negative reference standard is representative of the tumor load in a subject that does not have the cancer; and the positive reference standard is representative of the tumor load in a subject that has the cancer, and an smDI of the DNA molecules in the sample that is statistically significantly greater than the negative reference standard, and/or is approximately the same the positive reference standard, indicates that the subject is likely to have the cancer. The method may be used to detect an early stage of cancer (at stage 1 or stage 2).

Such a method may be also be used to stage a cancer in the subject. In this embodiment, the negative reference standard is representative of the tumor load in a subject that does not have the cancer, or has an early stage cancer, and the positive reference standard is representative of the tumor load in a subject that has a later stage cancer. An smDI that is approximately the same as the negative standard indicates that the subject is likely to have an early stage cancer, and an smDI that is statistically significantly greater than the negative reference standard, or is approximately the same as the positive standard, indicates that the subject is likely to have a more advanced stage of the cancer.

Such a method may also be used to determine if a tumor is benign or malignant. In this embodiment, the negative reference standard is representative of the tumor load in a subject that has a benign tumor, and the positive reference standard is representative of tumor load in a subject that has a malignant cancer. An smDI that is approximately the same as the negative standard indicates that the subject is likely to have a benign tumor, and an smDI that is statistically significantly greater than the negative reference standard, or is approximately the same as the positive standard, indicates that the subject is likely to have a malignant tumor.

Such a method may also be used to monitor the progress or prognosis of a cancer in a subject. In this embodiment, the smDI is determined at various times during the course of the cancer. A decrease in the smDI over the course of the analysis indicates that cancer is going into remission and that the prognosis is likely to be good, and an increase in the smDI over the course of the analysis indicates that cancer is progressing and that the prognosis is not likely to be good.

Such a method may also be used to evaluate the efficacy of a cancer treatment. In this embodiment, the smDI is measured at different times during the treatment. In one embodiment of the invention, a decrease in the smDI over the course of the analysis indicates that the cancer treatment is efficacious, and an increase in the smDI over the course of the analysis indicates that the cancer treatment is not efficacious.

In any of the methods of the invention, the fluorescent dye may be an intercalating dye (such as, e.g., TOTO-3); covalently bound to the DNA through a coupling reaction; introduced into the DNA though an enzymatic reaction (such as PCR); or incorporated into the DNA by the binding of a labeled fluorescent probe (such as, e.g., a Cy5-labeled oligonucleotide probe). The method may be high throughput. The subject may be human. DNA in the sample may not be separated from other components in the sample. The cancer may be ovarian, breast, lung, prostate, colorectal, esophageal, pancreatic, prostate, head and neck, gastrointestinal, bladder, kidney, liver, lung, or brain cancer, gynecological, urological or brain cancer, or a leukemia, lymphoma, myeloma or melanoma. The cell-free body fluid sample may be generated from a pleural effusion, ascites sample, plasma, serum, whole blood, urine, ductal lavage or sputum.

A method of the invention may further comprise introducing a fluorescent tracer particle during single molecule spectroscopy to control for flow velocity, focus position and/or fluorescent intensity.

Another aspect of the invention is a kit for carrying out a method of the invention, comprising a disposable microfluidic device preloaded with a buffer; tracer particles, such as, e.g., 0.04 µm yellow-green fluorescent microspheres, and/or a suitable fluorescent dye, such, e.g., as TOTO-3.

Another aspect of the invention is a method for determining the size distribution of DNA molecules in a sample, comprising labeling the DNA molecules in the sample with a fluorescent dye in a stoichiometric manner, subjecting the labeled DNA to single molecule cylindrical illumination confocal spectroscopy (CICS), such that a uniform detection profile is produced, and analyzing fluorescent burst parameters of the labeled DNA, wherein the fluorescent parameters, burst size, burst height and/or transit time, indicate the length of each of the DNA molecules; and the fluorescent burst rate indicates the abundance of each size of DNA molecule, and conducting single molecule DNA integrity analysis (smDIA) of the labeled DNA molecules in the sample.

In one embodiment of this method, the CICS is conducted in a cylindrical illumination confocal spectroscopy system as described in Example III.

A "cell-free" DNA, as used herein, is DNA (genomic or mitochondrial) that has been released or otherwise escaped from a cell into blood or other body fluid in which the cell resides. Some samples (e.g., serum or plasma samples) comprising cell-free DNA can be analyzed in a method of the invention without further separations or purification, because, under the conditions of the assay, there will be little if any contaminating DNA that can interfere with an assay of the invention. For example, when a cell membrane impermeant dye is used, the presence of intact cells in a sample will not interfere with the specific detection of cell-free DNA, because DNA located inside of those cells will not be labeled. For other samples, it may be necessary to remove DNA present in contaminating cells or cellular debris by removing such cells or cellular debris before subjecting the DNA to a method of the invention.

Suitable subjects from which the body fluids can be collected include any animal which has, or is suspected of having, a cancer, such as vertebrate animals, e.g. mammals, including pets, farm animals, research animals (mice, rats, rabbits, guinea pigs, etc) and primates, including humans.

Any of a variety of suitable body fluids for analysis will be evident to a skilled worker. The cell-free DNA can be found in circulating body fluids, such as blood, but it can also be found in non-circulating fluids, such as urine, sputum, bile juice, etc. Suitable body fluids include, e.g., blood (e.g., whole blood, plasma or serum), lymph fluid, serous fluid, a ductal aspirate sample or ductal lavage, bronchoalveolar lavage, a lung wash sample, a breast aspirate, a nipple discharge sample, peritoneal fluid, duodenal juice, pancreatic duct juice, bile, an esophageal brushing sample, glandular fluid, amniotic fluid, cervical swab or vaginal fluid, ejaculate, semen, prostate fluid, cerebrospinal fluid, a spinal fluid sample, a brain fluid sample, lacrimal fluid, tears, conjunctival fluid, synovial fluid, saliva, stool, sperm, urine, sweat, fluid from a cystic structure (such as an ovarian cyst), nasal swab or nasal aspirate, or a lung wash sample.

It will be evident to a skilled worker what source of body fluid is suitable for the detection of a particular type of cancer. For example, for ovarian cancer, suitable samples can be generated from, e.g., a pleural effusion, ascites fluid (effusion in the abdominal cavity), plasma, urine or sputum. For the detection of pancreatic cancer, one can assay, e.g., pancreatic duct juice (sometimes referred to as "pancreatic juice" or "juice"), for example obtained during endoscopy, brushings of the pancreatic duct, bile duct or aspirates of cyst fluid. For the detection of lung cancer, sputum or bronchoalveolar lavage can be used. For head and neck cancer in the oral or pharyngeal cavity, sputum or wash from the mouth can be used. For colon cancer, prostate cancer, breast cancer and nasopharyngeal cancer, suitable body fluids include stool, prostate fluid, breast aspirate and nasal swab/wash, respectively.

In some cases, a body fluid sample is treated to remove cells, cellular debris and the like. For example, a urine sample, a pleural effusion or an ascites sample can be subjected to centrifugation, following conventional procedures, and the supernatant containing the DNA isolated; or a sample can be filtered to remove the cells or cell debris. In other cases, e.g., when serum is used, no further treatment is required to remove cells, cellular debris and the like.

"Cell-free" body fluids used in a method of the invention are body fluids into which DNA from cancer cells, e.g. tumors, has been released, and from which all or substantially all particulate material in the preparation, such as cells or cell debris, has been removed. These samples are sometimes referred to herein as cell-free "effusion samples." It will be evident to a skilled worker that a cell-free body fluid generally contains only a few if any cells, but that a number of cells can be present in a "cell-free" body fluid, provided that those cells do not interfere with a method of the invention. A skilled worker will recognize how many cells can be present without interfering with the assay. For example, 1,000 or fewer cells (e.g., 1, 10, 50, 100, 500 or 1,000 cells) can generally be present in a volume of one liter of body fluid without interfering with the assay.

Methods for preparing a DNA sample from a body fluid (e.g., a cell-free body fluid) are conventional and well-known in the art. It may be desirable to include an agent in the sample which inhibits DNase activity. For example, for the isolation of DNA from a plasma sample, anti-coagulants contained in whole blood can inhibit DNase activity. Suitable anti-coagulants include, e.g., chelating agents, such as ethylenediaminetetraacetic acid (EDTA), which prevents both DNase-caused DNA degradation and clotting of whole blood samples.

If desired (although generally not necessary), DNA for analysis can be isolated (purified), before subjecting it to a method of the invention, using conventional methods or kits that are commercially available. Methods for isolating DNA and other molecular biology methods used in the invention can be carried out using conventional procedures. See, e.g., discussions in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. (current edition) *Current Protocols in Human Genetics*, John Wiley & Sons, Inc.; and Coligan et al. (current edition) *Current Protocols in Protein Science*, John Wiley & Sons, Inc.

DNA molecules can be labeled with a fluorescent dye in a stoichiometric manner (such that the amount of label is proportional to the length of the DNA molecules) by any of a variety of methods, which will be evident to a skilled worker. Such methods include, e.g., using an intercalating dye, covalently binding the dye to the DNA through a coupling reaction, introducing the dye into the DNA by an enzymatic method (such as PCR), or incorporating the dye into the DNA by the binding of a labeled fluorescent probe, such as an oligonucleotide, antibody, or aptamer, PNA, LNA etc.

Any of a variety of fluorescent dyes can be used, as will be evident to a skilled worker. Intercalating dyes are often used due to ease and their useful properties. Other types of dyes can also be used, however. Desirable (but not essential) properties of a suitable fluorescent dye include that it exhibits signal enhancement upon incorporation into the DNA (so that the unincorporated label will not give rise to background fluorescence), preferential binding to DNA, cell membrane impermeance, emits at a level that is far from biological autofluorescence (thus reducing background), provides stoichiometric binding even when concentrations are accurately controlled (i.e., is tolerant to a wide range of staining ratios), and exhibits fast on rate kinetics (for a short reaction time) and slow off rate kinetics (so it can be diluted). Representative dyes that can be used include the intercalating dyes TOTO-3, PicoGreen, EvaGreen and YOYO-1. Other suitable dyes are described in the following world wide web sites: invitrogen.com/site/us/en/home/References/Molecular-Probes-The-Handbook/tables/Properties-of-classic-nucleic-acid-stains.html; invitrogen.com/site/us/en/home/References/Molecular-Probes-The-Handbook/tables/Specialty-nucleic-acid-reagents-for-molecular-biology.html; invitrogen.com/site/us/en/home/References/Molecular-Probes-The-Handbook/tables/Cell-membrane-impermeant-cyanine-nucleic-acid-stains.html; and invitrogen.com/site/us/en/home/References/Molecular-Probes-The-Handbook/tables/Cell-permeant-cyanine-nucleic-acid stains.html.

As used herein, with regard to single molecule spectroscopy, the term "burst size" means the integrated or total number of photons emitted by a single molecule within a fluorescent burst; the term "burst height" means the maximum number of photons emitted by a single molecule within a single acquisition period of a fluorescent burst; and the term "burst rate" means the rate at which individual fluorescent bursts are detected. The term "smDI" means single molecule DNA integrity, and is defined as the number of detected bursts arising from large DNA of a predetermined range divided by the number of bursts arising from small DNA of a second predetermined range. The size of the DNA molecule is determined via the fluorescent burst sizing analysis, and the relative abundance is determined by direct burst counting. μCICS analysis is performed on labeled DNA molecules to obtain single molecule trace data. Fluorescent bursts are identified in the single molecule trace data using a thresholding algorithm. The identified bursts are analyzed to determine burst parameters such as burst size, burst height, and transit time. A calibration curve is then used to correlate the burst parameters with DNA size such that each burst can be attributed to a DNA molecule of specific length. Finally, smDI is calculated by tallying the number of bursts within the predetermined ranges where smDI=# of large DNA fragments detected/# of small DNA fragments detected.

Methods of single molecule spectroscopy are well-known in the art. In one embodiment of the invention, the single molecule spectroscopy is cylindrical illumination confocal spectroscopy (CICS) or microfluidic cylindrical illumination confocal spectroscopy (μCICS). The Examples herein describe methods using these approaches. For additional guidance as to how to carry out CICS or μCICS, see Liu et al. (2008) *Biophys J* 95, 2964-2975, the Examples herein, or co-pending U.S. application Ser. No. 12/612,300, filed on Nov. 4, 2009. When single molecule spectroscopy is carried out using flow cytometry, a method of the invention is carried out essentially as described herein using CICS, except the sample is loaded into a molecular cytometer which uses a hydrodynamic sheath flow to confine the molecules to the uniform region of the laser excitation (see, e.g., Habbersett et al. (2004) *Cytometry A* 60(2), 125-34). When single molecule spectroscopy is carried out using nanochannels, a method of the invention is carried out essentially as described herein using CICS, except the sample is loaded into a microfluidic device having channels significantly smaller (250 nm×250 nm w×h) than the size of the diffraction limited laser focus (1 um×2 um w×h). See, e.g., Foquet et al. (2002) *Anal Chem* 74, 1415-1422. The laser is focused into the center of the microchannel and DNA is flowed through accordingly.

In a method of the invention, a suitable cut-off value or range of values of DNA sizes is generally selected in order to distinguish between two populations of subjects. A person of ordinary skill in the art will be able to determine a suitable cut-off value of DNA size for, for example, distinguishing between subjects that have or do not have a particular type or stage of cancer, using empirical methods, without undue experimentation. This cut-off value will depend on a variety of factors including, e.g., biological factors, such as the type of cancer, location of tumor, clinical stage, type of sample that the CNAs are obtained from, treatments being performed, pre-existing underlying non-neoplastic disease, concurrent physiological factors such as trauma and other diseases; and engineering factors, such as the measurement of CV, pre-analytical factors (freshness of sample, freeze-thaw cycles, sample collection and processing steps), and system signal to noise ratio. The cut-off value can be, e.g., about 200, 300, 400, 500, 600, 700, 800, 900, 1,000 or greater number of base pairs. For example, for the lung cancer study shown in Examples I and II herein, the optimal cut-off value is determined to be 800 bp. Alternatively, one can distinguish between values that lie within particular ranges of sizes of DNAs. For example, values of 200 bp or lower (e.g., about 100-200 bp) can be selected to correspond to subjects that do not have a cancer, and values from 400 bp or greater (e.g., about 400-800 bp) can be selected to correspond to subjects that have a cancer.

Figure 3:
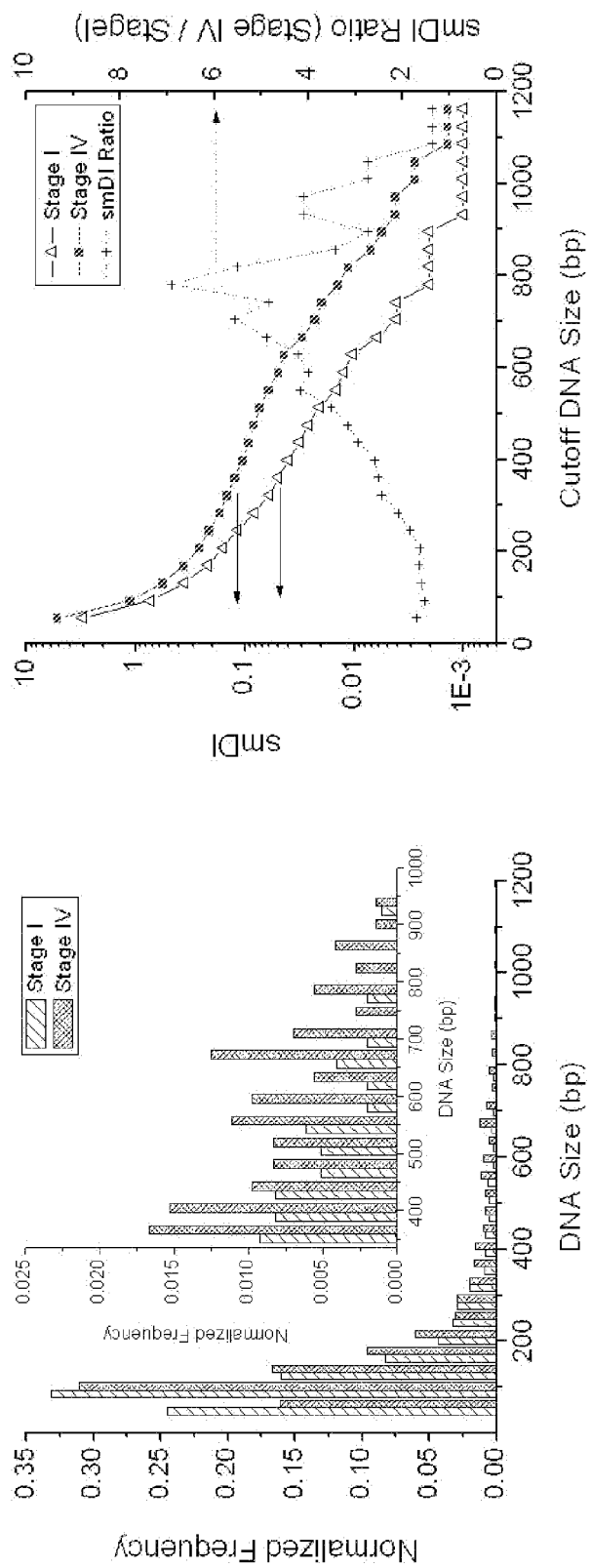
FIG. 3A shows DNA sizing histograms of serum CNAs taken from a stage I and stage IV lung cancer patient. At DNA lengths <320 bp, the two patient CNA samples appear similar. However, at DNA sizes >320 bp, the stage IV shows a higher prevalence of larger DNA. Inset shows a close-up view of the 320-1000 bp region.
FIG. 3B shows single molecule DNA integrity (smDI) marker values for the patients shown in FIG.

In one embodiment of the invention, the distinction between the number of long and short bursts (a single molecule DNA integrity (smDI) value) can be defined empirically, without undue experimentation, as a predetermined cutoff value or range of values. For example, if one selects DNA sizes from 0-200 bp to represent normal subjects, and a value of 400 or greater by to represent as subject that has a cancer, the smDI will be approximately 0 for a normal subject (no DNA molecules will be present that are greater than 400 bp), so a value of greater than about 0.04, 0.06, 0.08, 0.10, 0.125, 0.15, 0.175, 0.2, 0.3, 0.4, 0.5, 0.6, 0.7, 0.8, 0.9, 1, 5, 10, 15, 50, 100 or higher, or suitable ranges between such values, will indicate that a subject has a cancer. Similarly, referring to the data in FIG. 3 herein, if one selects a DNA size cut-off value of 400 bp, an smDI of 0.04 indicates that the subject has stage I lung cancer, and an smDI of 0.10 indicates that the subject has stage IV lung cancer. Suitable predetermined smDI values will vary in accordance with a variety of factors, including, e.g., heterogeneity among patients, treatment status, tumor load, measurement resolution and sensitivity, sample preparation methods, cancer type, sample type, etc.

A method of the invention can be used for a variety of assays, including diagnosing a cancer (a malignant tumor, neoplasm, malignancy) in a subject, determining the stage of the cancer, determining the prognosis of a subject having a cancer (e.g., the likelihood of recurrence), or monitoring therapeutic efficacy of a drug or treatment regimen. A method of the invention is sensitive enough to allow for the early detection of cancers. A method of the invention is non-specific and sensitive to all tumors, regardless of type. Examples of suitable cancers will be evident to a skilled worker, and include, e.g., ovarian, breast, lung, prostate, colorectal, esophageal, pancreatic, prostate, gastrointestinal, bladder, kidney, liver, lung, head and neck (including oral cavity), gynecological, urological, or brain cancer, or leukemias, lymphomas, myelomas or melanomas. Metastatic spread can also be detected, since the method is sensitive to all neoplastic growths.

One embodiment of the invention is a general method for determining the tumor load in a subject, in which, rather than using predetermined, absolute values of smD1 to determine if, for example, a subject has a cancer, the smDI is compared to positive and/or negative reference values. "Tumor load," sometimes called tumor burden, refers to the number of cancer cells, the size of a tumor, or the amount of cancer in the body. This method comprises analyzing a body fluid sample from the subject by a method of the invention, and the single molecule DNA integrity analysis (smDIA) comprises correlating substantially quantized light pulses with the lengths of the DNA molecules detected, and calculating the single molecule DNA integrity (smDI) of DNA molecules in the sample. The method further comprises comparing the smDI of the DNA molecules in the sample to a positive and/or a negative reference standard, wherein the negative and positive reference standards are representative of defined amounts of tumor load.

For example, one embodiment of the invention is a method for determining if a subject is likely to have a cancer. In this method, a "positive reference standard" reflects (represents, is proportional to) the smDI in the same type of body fluid of a subject, or the average (e.g., mean) value for a population or pool of subjects, that have the cancer being tested for. In one embodiment of the invention, an smDI value that is approximately the same as (e.g., statistically the same as) a positive reference standard is indicative of the cancer. A "negative reference standard," as used herein, reflects (represents, is proportional to) the smDI of DNA from the same type of cell-free body fluid of a subject, or the average (e.g., mean) value for a population or pool of subjects, that do not exhibit clinical evidence of the cancer of interest. Such "normal" controls do not have the cancer being tested for, or any type of cancer, or have a benign tumor of the type of cancer being assayed for. An smDI value that is greater than (e.g., statistically significantly greater than) the negative reference standard is indicative of the cancer.

By "likely" is meant herein that the subject has at least about a 75% chance (e.g., at least about a 75%, 80%, 85%, 90%, 95% chance) of having the cancer.

In one embodiment of the invention, the positive and negative reference standards are measured from subjects or pools of subjects, or are retrospective values from such subjects. Alternatively, and more conveniently, a positive or negative reference standard can comprise an artificial mixture of DNA molecules of varying length that will give rise to predetermined smDI expected of a subject that does, or that does not, have the cancer, respectively. Such a DNA mixture can be prepared synthetically. In one embodiment, the smDI is the same as expected in a subject having the cancer being assayed for (positive reference standard), or not having the cancer being assayed for (negative reference standard). In another embodiment, the smDI in the reference standard is proportional to the amount expected in a subject having, or not having, the cancer being assayed, and the investigator applies a suitable multiple to convert the standard to the actual expected value.

By "statistically significant" is meant a value that is reproducible or statistically significant, as determined using statistical methods that are appropriate and well-known in the art, generally with a probability value of less than five percent chance of the change being due to random variation. For example, a significant increase in the smDI can be at least about a 25% or 50% increase, or at least 2-fold (e.g., at least about 5-fold, 10-fold, 15-fold, 20-fold, 25-fold, 30-fold, 100-fold, or more) higher than a negative reference standard. The degree of increase can be a factor of a number of variables, including the type and stage of the cancer, the age and weight of the subject, and the like.

A diagnostic method of the invention can be used in conjunction with other, secondary, methods for diagnosing a cancer. For example, one can evaluate allelic imbalance, e.g. by using digital SNP assays (as described, e.g., by Chang et al. (2002) *Clin Cancer Res* 8, 2580-2585); conventional cytology analysis (as described, e.g., by Motherby et al. (1999) *Cytopathol* 20, 350-357; detection of mutations associated with the cancer (as described, e.g., by Parrella et al. (2003) *Mod Pathol* 16, 636-640), including a point mutation, a microsatellite alteration, a translocation, promoter methylation and/or the presence of a viral sequence; or determination of the amount of amplification of other amplified genomic loci [e.g., for ovarian cancer, the markers described by Nakayama et al. (2007) *Int J Cancer* 120, 2613-2617), or secretory tumor-associated markers (Borgono et al. (2004) *Mol Cancer Res* 2, 257-80; I. Shih (2007) *Hum Immunol* 68, 272-276; Shih et al. (2007) *Gynecol Oncol* 105, 501-7)]. Other molecular assays, including PCR-based assays, will be evident to a skilled worker (see, e.g, Fiegl et al. (2004) *J Clin Oncol* 22, 474-83). Secondary assays such as those discussed above can be carried out before a length integrity assay of the invention, as part of a preliminary screen; at the same time as an assay of the invention is carried out; or after the assay is carried out.

Another aspect of the invention is a method for staging a cancer in a subject by a method of the invention. In this method, reference standards can be used that are representative of the smDIs of two or more subjects having different stages of the cancer. For example, a negative smDI can be used that represents the tumor load in a subject that does not have the cancer, or has an early stage cancer, and the positive reference standard is representative of the tumor load in a subject that has a late stage cancer. An smDI that is approximately the same as the negative standard indicates that the subject is likely to have an early stage cancer, and an smDI that is statistically significantly greater than the negative reference standard, or is approximately the same as the positive standard, indicates that the subject is likely to have a more advanced stage of the cancer. See, e.g., the staging of stage I or stage IV lung cancer in the Examples herein. The method can be used to screen a non-symptomatic subject, or a subject having early stage cancer, in order to detect whether a subject has a curable form of the cancer, such a stage 1 or stage 2 cancer. The detection in the sample of an elevated smDI would indicate a high probability of cancer and, in the case of an asymptomatic subject, necessitate a search for the cancer.

Another aspect of the invention is a diagnostic method for determining if a tumor in a subject is benign or malignant, comprising measuring DNA in a body fluid (e.g., a cell-free body fluid) from the subject by a method of the invention. A benign tumor will give rise to a lower smDI for the tested DNA in the body fluid of the subject than will a malignant tumor.

Another aspect of the invention is a method for monitoring the progress or prognosis of a cancer in a subject, comprising measuring DNA in a body fluid (e.g., a cell-free body fluid) from the subject by a method of the invention at various times during the course of the cancer.

Another aspect of the invention is a method for evaluating the efficacy of a cancer treatment of a subject (e.g., chemotherapy, radiation, biotherapy or surgical operation), comprising measuring DNA in a body fluid (e.g., a cell-free body fluid) from the subject by a method of the invention, at different times during the course of the treatment (e.g., before, during, and/or after the treatment). It will be evident to an investigator that the smDI may actually increase temporarily during an efficacious treatment, because during the treatment the cancer cells are dying and, once the treatment is completed, the smDI value is expected to drop below the pre-treatment value. Whether the smDI increases or decreases during various stages of an efficacious treatment may also depend on other factors, such as, e.g., type of therapy (resection, chemotherapy, radiotherapy, etc.).

Methods of the invention can be readily adapted to a high throughput format, using automated (e.g. robotic) systems, which allow many measurements to be carried out simultaneously. Furthermore, the methods can be miniaturized.

The order and numbering of the steps in the methods described herein are not meant to imply that the steps of any method herein must be performed in the order in which the steps are listed or in the order in which the steps are numbered. The steps of any method disclosed herein can be performed in any order which results in a functional method. Furthermore, the method may be performed with fewer than all of the steps, e.g., with just one step.

The phrase "a method for diagnosing" a cancer in a subject . . . " is not meant to exclude tests in which no cancer is found. In a general sense, this invention involves assays to determine whether a subject has cancer, irrespective of whether or not such a cancer is detected.

Any combination of the materials useful in the disclosed methods can be packaged together as a kit for performing any of the disclosed methods. For example, a kit of the invention can contain a disposable microfluidic device preloaded with a buffer such as TE buffer, tracer particles such as 0.04 µm yellow-green fluorescent microspheres, and/or fluorescent dye such as TOTO-3. If desired, defined amounts of positive and negative standards (e.g., prepared synthetically) can be included. If desired, the reagents can be packaged in single use form, suitable for carrying one set of analyses.

Kits may supply reagents in pre-measured amounts so as to simplify the performance of the subject methods. Optionally, kits of the invention comprise instructions for performing the method. Other optional elements of a kit of the invention include suitable buffers, labeling reagents, packaging materials, etc. The kits of the invention may further comprise additional reagents that are necessary for performing the subject methods. The reagents of the kit may be in containers in which they are stable, e.g., in lyophilized form or as stabilized liquids.

In the foregoing and in the following example, all temperatures are set forth in uncorrected degrees Celsius; and, unless otherwise indicated, all parts and percentages are by weight.

EXAMPLES

Example I

Materials and Methods

DNA Sizing Calibration.

λ Hind III digest DNA (New England Biolabs) was used as a control sample for assay development. To prepare the sample for analysis, the DNA was diluted to 200 ng/mL, mixed with 0.1 µM TOTO-3 dye (Invitrogen), and allowed to incubate at room temperature in the dark for 1 hour. The sample was then further diluted to 1 pM and loaded into the microfluidic device for analysis. All dilutions were performed using TE buffer.

µCICS Analysis.

µCICS analysis was performed using the previously described platform (Liu et al. (2008) *Biophys J* 95, 2964-2975). PDMS microfluidic devices were fabricated with standard soft-lithography techniques. Each microfluidic device contains a large transport channel with a centrally located analysis constriction. The analysis constriction measures 20×5×1.5 µm or 20×5×0.5 µm (l×w×h). The device also contains a filter array at the inlet to remove particles and cells to reduce channel clogging. Samples were driven through the device using a constant pressure source controlled by a series of precision gas regulators. Flow velocity and stability was monitored using fluorescent tracer particles as described below. A 633 nm He—Ne laser was used to excite the TOTO-3 labeled DNA molecules while a 488 nm Ar-ion laser was used to excite the fluorescent tracer particles. Piezoelectric stages were used to focus the µCICS laser into the center of the analysis constriction. Each acquired single molecule trace consists of 5 minutes of data collected with a 0.1 ms bin time. 0.8 mW and 2.3 mW of blue and red laser power were used unless otherwise indicated. Excitation laser power was measured at the laser fiber output.

Fluorescent Tracer Particle.

0.04 µm yellow-green Fluospheres (Molecular Probes) were mixed into each sample immediately before analysis and used to monitor sample flow velocity. A yellow-green polystyrene bead was chosen to fluoresce at a wavelength far from TOTO-3 to minimize spectral leakage. The stock solution was first diluted 1000× in TE buffer. 2 µl of the diluted bead solution was then added to each sample. For each sample, the drive pressure was adjusted until a particle transit time of 5 ms was achieved. This ensured that the flow velocity remained constant across experiments, chips, and samples. Typical drive pressures range from 0.01-4 psi depending on specific device geometry. A typical calibration curve of applied pressure versus particle transit time is depicted in FIG. 6. Slow flow velocities were used to reduce Poisson variability and increase detection sensitivity.

Clinical Sample Analysis.

20 µL of patient serum sample was mixed with 20 µL of 0.1 µM TOTO-3 dye. The samples were allowed to react for 1 h after which they were diluted 150× in TE buffer. Fluorescent tracking particles were then added to the diluted sample, and the sample loaded into the µCICS system for analysis. The flow velocity was adjusted to obtain a particle transit time of 5 ms. DNA sizing was performed after a stable flow velocity was obtained. 2.3 mW of laser excitation power, 0.1 ms bin time, and a 20×5×0.5 µm (l×w×h) microchannel were used. Data was acquired for 5 minutes for each trace.

Data Analysis.

A thresholding algorithm was applied to each single molecule trace to identify fluorescent bursts. A threshold of 40 photons was used unless otherwise indicated. This threshold was a minimum of 3 σ greater than the average background level to ensure high confidence burst identification. The identified bursts were then histogrammed and curve fit using Origin.

In Vitro DNA Fragmentation.

The ability of CICS to characterize DNA integrity was tested using an in vitro model of DNA fragmentation. λ DNA (Invitrogen) was sheared into random length fragments by exposure to ultrasonic agitation (Branson) for 0, 15, 60, 120, or 600 seconds. The DNA fragments were then labeled using TOTO-3 and analyzed on the CICS platform at a total DNA concentration of 0.2 ng/mL. As the ultrasonic agitation time increased, the DNA became increasingly fragmented (i.e. decreased DNA integrity) and variable in length. FIG. 4 shows 5 burst size histograms of the ultrasonically sheared DNA. The control DNA (0 min) appears as a sharp Gaussian shaped peak due to the uniform size distribution of the λ DNA. As the ultrasonic shearing time increases, the sharp peak representing intact λ DNA decreases in size and broadens in width while the broad distribution representing small background bursts increases in size. At 600 seconds, the DNA is entirely sheared and no large DNA pieces remained. This can be quantitatively seen by examining the burst size as function of ultrasonic agitation time as shown in Table 1.

TABLE 1

Characterization of Ultrasonically Fragmented DNA using CICS

| Shearing Time (s) | Detected Bursts | Average Burst Size (photons) |
|---|---|---|
| 0 | 2309 | 17022 ± 16776 (99%) |
| 15 | 3384 | 13816 ± 15451 (112%) |
| 60 | 3797 | 11111 ± 14038 (126%) |
| 120 | 5773 | 7487 ± 14038 (152%) |
| 600 | 17514 | 494 ± 560 (113%) |

The average burst size progressively decreases while the CV increases with increasing agitation time, representing both decrease in average fragment size and an increased variability in the distribution of fragment sizes. By 600 s the CV decreases again because the large DNA are entirely fragmented and there is no longer a mixed population of small and large DNA. It can also be seen that detected number of DNA fragments increases proportionately to the decrease in average fragment size as expected. The disparity between average burst size of total DNA versus the λ peak alone is due to the presence of small DNA fragments that are present in even the 0 s sample. This is due to sample impurity or degradation which we have found to differ between sample vendors. Only 1 pg of DNA was analyzed in each BSDA histogram. In contrast, these differences cannot be easily seen or quantified using gel electrophoresis (FIG. 5) which requires 1000× more DNA for analysis.

Example II

Results

Single molecule DNA sizing of λ Hind III digest DNA was performed via fluorescent burst size analysis. The DNA was stoichiometrically labeled with TOTO-3 intercalating dye such that each DNA molecule incorporated a number of dye molecules that was directly proportionate to its length. The labeled DNA sample was then diluted, fluorescent tracer particles were added, and the sample was loaded into a microfluidic device for µCICS analysis. The µCICS platform has two excitation and detection channels. 488/520 nm excitation/detection was used to monitor the tracer particle fluorescence while 633/670 nm excitation/detection was used to analyze the DNA fluorescence. The fluidic drive pressure was slowly changed until an average tracer particle transit time of 5 ms was obtained. This corresponds to an average flow velocity of 0.2 mm/s within the microchannel.

To perform a measurement, the µCICS observation volume is focused into the center of the 5 µm wide analysis constriction. The 7 µm wide observation volume is designed to be slightly larger than the analysis constriction to ensure 100% mass detection efficiency, straightforward alignment, and detection uniformity. As each labeled DNA molecule traverses the µCICS observation volume, it is excited and emits a burst of photons. This procession of fluorescent signals is collected as a function of time to create a single molecule trace. Because the observation volume is uniform across the width of the channel, the size of each fluorescent burst can be directly correlated to the length of the DNA and the number of dye molecules contained therein. A thresholding algorithm is used to distinguish fluorescent bursts from background in the single molecule trace. The identified fluorescent bursts are then stored and analyzed for burst parameters such as burst size, burst width, and transit time.

Figure 1:
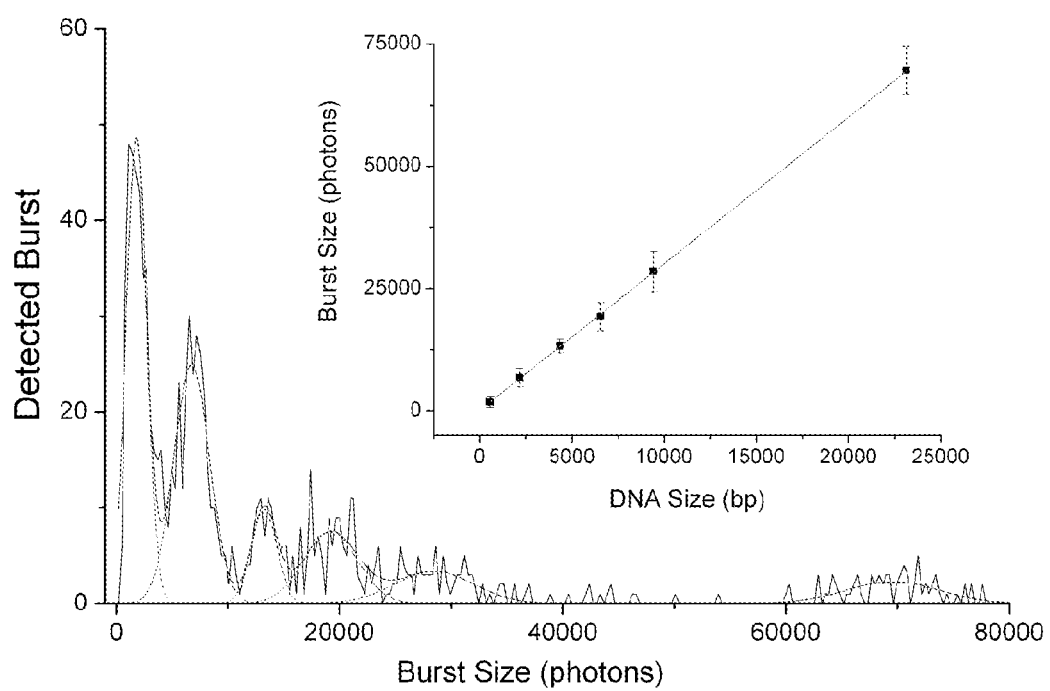
FIG. 1 shows a fluorescent burst size histogram of λ Hind III digest DNA taken using μCICS in a 0.5 μm deep constriction. Each peak in the histogram corresponds to a fragment population in the digest. The total histogram is composed on ~1063 DNA molecules. The 125 bp peak cannot be seen due to the low signal intensity while the 2027 bp and 2322 bp peaks cannot be individually resolved due to the measurement CV. Gaussian fits, shown in green, were used to identify peak center locations and measurement CVs. (inset) The peak center locations show the expected linear correlation to DNA size ($R^2$=0.9997).

For burst size analysis, the bursts are histogrammed as shown in FIG. 1. Each peak in the histogram is a collection of fluorescent bursts that corresponds to a sub-population of DNA within the Hind III digest. When the peaks are curve-fit with a series of Gaussian functions, a linear correlation can be seen between average burst size (i.e. peak center position) and DNA length. As has been previously described (Habbersett et al. (2004) *Cytometry A* 60, 125-134), the measurement CV increases as DNA size decreases due to Poisson variability in staining and the photoemission and -detection process. Although burst size is used as the measurand in this assay, µCICS can be used other nanosensor assays to accurately determine burst rate, FRET efficiency, coincidence rates, and fluorescent intensity.

Figure 2:
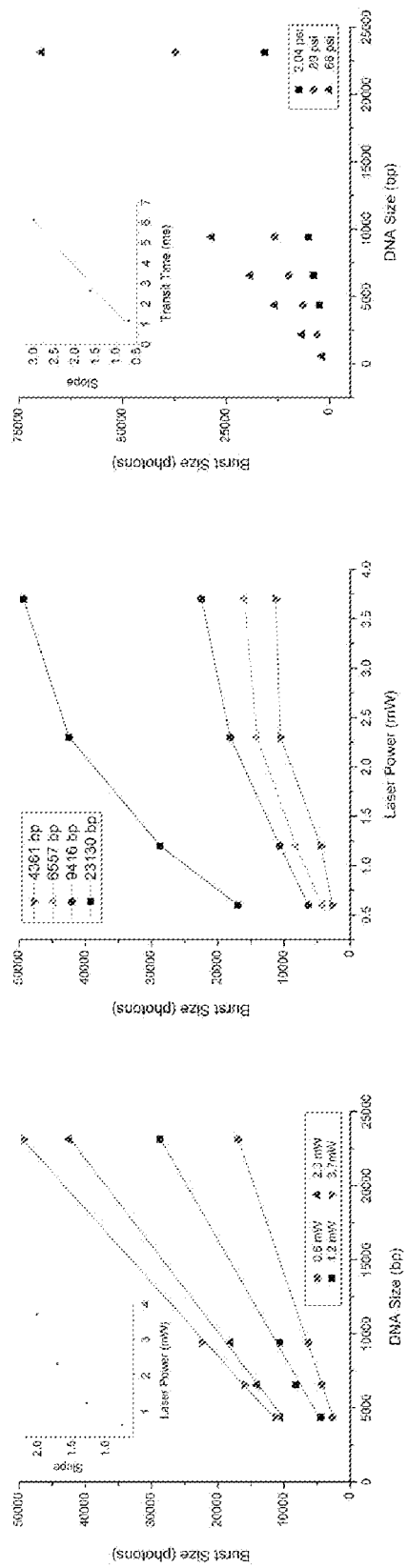
FIG. 2 shows laser power and flow velocity effects on μCICS fluorescent burst sizing of λ Hind III digest DNA. Each linear fit was taken from a burst size histogram consisting of at least 1000 peaks. Sizing was performed in either a 1.5 μm (a+b) or 0.5 μm (c) deep constriction.

Three critical operating parameters in obtaining µCICS burst parameter data are laser excitation power, sample flow rate, and constriction size. To obtain maximal signal-to-noise ratio and the lowest measurement CV, the laser power should be adjusted to just below optical saturation of the fluorophore being analyzed. To test this, DNA sizing histograms were taken while the laser power was changed from 0.6 mW to 3.7 mW. As seen in FIG. 2A, the dependency of burst size on DNA size becomes steeper as the laser power is increased. The steeper slope and lower measurement CV at higher laser powers result in higher DNA sizing resolution (FIG. 6) Interestingly, when this slope is plotted against laser power, the increase is not linear and shows saturation effects (FIG. 2A inset). This is evident in FIG. 2B where the burst size of each fragment is shown as a function of laser power. Because the sample contains individual populations of DNA molecules of disparate brightness but same color, it can be seen that each population optically saturates at a different laser power. Intuitively, longer DNA fragments containing more individual TOTO-3 dye molecules saturate at higher laser powers than shorter DNA with less dye. Thus, the laser power can only be optimally set for a single fragment population or, more generally, a single fluorophore within the mixture being analyzed. This can have implications when multiplex analysis is performed with mixtures of fluorescent labels.

Sample flow rate can have a significant impact on burst parameter data and must be optimized in conjunction with the laser excitation power. It must not only be optimized but also stable throughout the course of a measurement. Many microfluidic systems use external pumps such as syringe pumps and peristaltic pumps to drive samples through the device. We have found when using elastomeric devices and syringe pumps at low flow rates that flow velocities can be highly unstable both on short (~30 s) and long time scales (~1 hour), particularly when changing flow rates. This can be attributed to the pulsatile nature of the pumping mechanism and the interaction of the constant flow volume drive mechanism with elastic deformation of the device. In contrast, constant pressure drive sources (e.g. hydrostatic head or gas pressure) can be used to greatly reduce these effects. They require very little settling time (~30 s) between flow rate adjustments and behave highly linearly (FIG. 7).

Generally speaking, slower flow rates lead to higher precision single molecule measurements. As shown in FIG. 2A, DNA sizing histograms were acquired at three different drive pressures to test the affect of flow velocity. As the flow velocity is decreased, smaller DNA fragments can be discerned from background due to an increase in signal-to-noise ratio and decrease in measurement CV, thus demonstrating the need for flow velocity optimization in single molecule assays. The correlation between DNA length and fluorescent burst size becomes steeper at lower flow rates enabling higher precision measurements (FIG. 2A inset). The flow velocity was set to longer molecular transit times to maximize signal intensity and minimize Poisson variability while remaining faster than molecule diffusion times.

A significant benefit of μCICS analysis is that detection uniformity, mass detection efficiency, detection sensitivity (i.e. signal-to-noise ratio), and sample throughput can be optimized to each specific assay application by altering the interplay between detection volume and constriction size. It was previously shown that single fluorophore sensitivity and 100% mass detection efficiency could be achieved in μCICS by coupling a 7×2 μm (w×h) detection volume with a 5×2 μm (w×h) microchannel (Liu et al. (2008, supra)). Here, DNA sizing histograms were taken using 0.5 μm or 1.5 μm deep analysis constrictions. Table 2 depicts measurement CVs for each DNA fragment population. The 1.5 μm deep constriction gives higher measurement CVs but allows higher sample, decreased likelihood for clogging, and lower drive pressures. For the subsequent clinical samples, 0.5 μm deep constrictions were used to obtain higher DNA sizing resolution.

TABLE 2

DNA sizing measurement CVs for 0.5 μm and 1.5 μm deep analysis constrictions.

| | Burst Size CV | |
|---|---|---|
| DNA Fragment | 0.5 μm | 1.5 μm |
| 2.2 kb | 28% | 41% |
| 4.4 kb | 11% | 16% |
| 6.6 kb | 16% | 12% |
| 9.4 kb | 15% | 19% |
| 23.1 kb | 7% | 19% |

Finally, we tested whether the μCICS DNA sizing assay could be used to rapidly analyze clinical CNAs in serum without DNA isolation or PCR amplification. TOTO-3 fluoresces in the deep red (660 nm), far away from most cellular autofluorescence (525 nm) and was used as a fluorescent probe for CNAs. It is also cell membrane impermeant and highly specific, ensuring that only cell-free nucleic acids will be labeled. Using the optimized DNA sizing parameters, a 1-step assay for analyzing cell-free DNA size was developed. Serum samples from two lung cancer patients were directly mixed with 0.1 μM TOTO-3 dye and allowed to react for 1 hour. The labeled serum samples were then diluted, mixed with fluorescent tracer particles, and loaded into a microfluidic device for analysis. A previously acquired λ Hind III digest DNA histogram was used as a calibration curve.

FIG. 3A shows DNA sizing histograms for Stage I and Stage IV lung cancer patients. These fluorescent bursts are attributed to CNA fragments freely found within their serum. Few background bursts are seen from sample autofluorescence or nonspecific adsorption of TOTO-3 to beads or serum proteins (FIG. 8). Qualitatively, it can be seen that the stage IV sample has a greater proportion of larger nucleic acid fragments than the stage I sample. Below 320 bp (~750 photons), the two curves appear similar. However, from 320-1000 bp, the stage IV sample consistently contains more DNA (FIG. 3A inset).

The digital nature of single molecule counting allows us to easily calculate DNA integrity (DI). DNA integrity is typically defined as the ratio of long DNA to short DNA and has been used as a marker in cancer management (Wang et al. (2003) *Cancer Research* 63, 3966-3968). Similarly, we can define single molecule DNA integrity (smDI) as long DNA bursts/short DNA bursts where the distinction between long and short is defined by a cutoff threshold. Accordingly, FIG. 3B shows smDI marker values for the previous patients as a function of DNA threshold value. This marker has the greatest distinguishing power when the threshold is set at ~800 bp. Here the stage IV patient has an smDIA value nearly 7× that of the stage I patient. While this sample size is much too small to draw any clinical conclusions from, it demonstrates that μCICS can be used as a rapid and easy alternative to PCR for quantitative CNA analysis. (quantitative burst counting)

Discussion

A single molecule DNA sizing assay based on fluorescent burst sizing and μCICS was developed to demonstrate the use of microfluidic single molecule spectroscopy for PCR-free CNA analysis. DNA sizing in this manner has been previously demonstrated using nanochannels, molecular cytometry, and 3D focal volume expansions. One benefit of μCICS analysis is that it retains high sensitivity and accuracy while using pressure driven flow and epitaxial illumination. This simple arrangement allows it to be generically incorporated with typical, continuous flow microfluidic systems as the detection portion of larger lab-on-a-chip systems We have recently combined this method with as emerging droplet technologies. The use of microfluidics also greatly reduces sample consumption and assay cost. During each 5 min acquisition period, less than 10 pL of serum, 1 pL of dye stock, and 5 pL of fluorescent beads were consumed. The most expensive consumable in the assay is the glass coverslip that the disposable PDMS device is bonded to.

Embodiments of this assay present additional advantages over traditional PCR-based other than those previously discussed. For example, nested qPCR can only be used to concurrently probe a limited number of DNA sizes and loci. This can present sampling errors, particularly when only a few genome equivalents of DNA are tested. The limited number of sampled loci may not be representative of the larger CNA population as a whole and lead to high variability. On the other hand, the limited DNA sizing resolution may also hinder the accuracy of the DI marker. μCICS directly measures CNA size of all fragments irrespective of sequence, without sampling bias or ensemble averaging, eliminating a potentially significant source of error.

Although single molecule DNA sizing was demonstrated, additional types of fluorescent nanosensors and probes can be used in conjunction with μCICS to detect gene specific mutations or epigenetic changes in CNA molecules that are indicative of disease. Fluorescent probes based on coincidence, FRET, and quenching may be used to analyze SNPs, mutation status, and methylation (see, e.g., Zhang et al. (2005) *Nat Mater* 4, 826-831; Bailey et al. (2009) *Genome Res* 19, 1455-1461; Yeh et al. (2006) *Nucleic Acids Res* 34, e35. Here, a single reagent, an inexpensive DNA intercalating dye was used as a fluorescent probe to detect and size CNA molecules. The high specificity of TOTO-3 to nucleic acids and the high fluorescent enhancement upon binding enabled separation-free analysis directly from serum. The elimination of DNA isolation and purification reduced potential bias introduced by these sample preparation steps and streamlined analysis. Although much research has focused on cancer diagnostics, novel probe technologies coupled with multiplexed labeling methods may provide PCR-free, non-invasive tools for CNA analysis in other areas such as fetal medicine and trauma.

Conclusion

We have detailed the development of a rapid and straight-forward assay for CNA analysis based on μCICS, a microfluidic single molecule spectroscopy technique. We initially surmised that the overlap in dynamic range between single molecule sensing and physiological CNA levels would enable direct analysis of CNA markers without PCR amplification. DNA integrity was chosen as an example of a promising cancer marker where the lack of alternatives to PCR-based methods may be limiting its validation. With proper assay design and probe selection, microfluidic single molecule spectroscopy can help rectify not only practical but also technical limitations of PCR detection. However, PCR and single molecule methods need not be mutually exclusive. We have previously combined the methods to achieve ultra-sensitive detection of methylation in cell-free DNA. Currently, a more exhaustive clinical study is being performed using μCICS to analyze cell-free DNA integrity to monitor tumor dynamics and disease progression. It is expected that single molecule methods can be used to speed the clinical translation and adoption of new CNA biomarkers.

Example III

System for CICS

The terms light, optical, optics, etc are not intended to be limited to only visible light in the broader concepts. For example, they could include infrared and/or ultraviolet regions of the electromagnetic spectrum according to some embodiments of the current invention.

An embodiment of the current invention provides a confocal spectroscopy system that can enable highly quantitative, continuous flow, single molecule analysis with high uniformity and high mass detection efficiency. Such a system will be referred to as a Cylindrical Illumination Confocal Spectroscopy (CICS) system. CICS is designed to be a highly sensitive and high throughput detection method that can be generically integrated into microfluidic systems without additional microfluidic components.

Rather than use a minute, diffraction limited point, CICS uses a sheet-like observation volume that can substantially entirely span the cross-section of a microchannel. It is created through the 1-D expansion of a standard diffraction-limited detection volume from approximately 0.5 fL to 3.5 fL using a cylindrical lens. Large observation volume expansions in 3-D (>100× increase in volume) have been previously performed to directly increase mass detection efficiency and to decrease detection variability by reducing the effects of molecular trajectory (Wabuyele, M. B., H. Farquar, W. Stryjewski, R. P. Hammer, S. A. Soper, Y. W. Cheng, and F. Barany. 2003. Approaching real-time molecular diagnostics: single-pair fluorescence resonance energy transfer (spFRET) detection for the analysis of low abundant point mutations in K-ras oncogenes. *J. Am. Chem. Soc.* 125:6937-6945; Habbersett, R. C., and J. H. Jett. 2004. An analytical system based on a compact flow cytometer for DNA fragment sizing and single-molecule detection. *Cytometry A* 60:125-134; Filippova, E. M., D. C. Monteleone, J. G. Trunk, B. M. Sutherland, S. R. Quake, and J. C. Sutherland. 2003. Quantifying double-strand breaks and clustered damages in DNA by single-molecule laser fluorescence sizing. *Biophys. J.* 84:1281-1290; Chou, H.-P., C. Spence, A. Scherer, and S. Quake. 1999. A microfabricated device for sizing and sorting DNA molecules. *Proceedings of the National Academy of Sciences* 96:11-13; Goodwin, P. M., M. E. Johnson, J. C. Martin, W. P. Ambrose, B. L. Marrone, J. H. Jett, and R. A. Keller. 1993. Rapid sizing of individual fluorescently stained DNA fragments by flow cytometry. *Nucl. Acids Res.* 21:803-806). However, these approaches often still require molecular focusing and/or unnecessarily compromise sensitivity since observation volume expansion in the direction of molecular travel is superfluous. For example, much pioneering work has been performed by Goodwin et al. in reducing detection variability through a combination of 3-D observation volume expansion (1 pL) and hydrodynamic focusing. While highly sensitive and uniform, these flow cytometry based methods use an orthogonal excitation scheme that is ill suited to incorporation with microfluidic systems. Chou et al., on the other hand, have performed a 3-D observation volume expansion to increase uniformity in an epi-fluorescent format for DNA sizing in a PDMS microfluidic device. The large size of the observation volume (375 fL) reduces signal-to-noise ratio and limits sensitivity to the detection of large DNA fragments (>1 kbp). Rather than a large 3-D expansion, a smaller 1-D expansion can be used to increase mass detection efficiency and increase detection uniformity while having a reduced effect on signal-to-noise ratio and detection sensitivity. 1-D beam shaping using cylindrical lenses has been recently applied in selective plane illumination microscopy (Huisken, J., J. Swoger, F. Del Bene, J. Wittbrodt, and E. H. K. Stelzer. 2004. Optical Sectioning Deep Inside Live Embryos by Selective Plane Illumination Microscopy. Science 305:1007-1009), confocal line scan imaging (Ralf, W., Z. Bernhard, and K. Michael. 2006. High-speed confocal fluorescence imaging with a novel line scanning microscope. *J. Biomed. Opt.* 11:064011), imaging-based detection of DNA (Van Orden, A., R. A. Keller, and W. P. Ambrose. 2000. High-throughput flow cytometric DNA fragment sizing. *Anal. Chem.* 72:37-41), and fluorescence detection of electrophoretically separated proteins (Huang, B., H. K. Wu, D. Bhaya, A. Grossman, S. Granier, B. K. Kobilka, and R. N. Zare. 2007. Counting low-copy number proteins in a single cell. *Science* 315:81-84) but have not been thoroughly explored in SMD. We present CICS as a confocal SMD system and method in which the trade-off between observation volume size, signal-to-noise ratio, detection uniformity, and mass detection efficiency can be easily modeled and optimized through 1-D beam shaping.

FIG. 9A is a schematic illustration of a cylindrical illumination confocal spectroscopy system 100 according to an embodiment of the current invention. The cylindrical illumination confocal spectroscopy system 100 includes a fluidic device 102 having a fluid channel 104 defined therein, an objective lens unit 106 arranged proximate the fluidic device 102, an illumination system 108 in optical communication with the objective lens unit 106 to provide light to illuminate a sample through the objective lens unit 106, and a detection system 110 in optical communication with the objective lens unit 106 to receive at least a portion of light that passes through the objective lens unit 106 from the sample. The illumination system 108 includes a beam-shaping lens unit 112 constructed and arranged to provide a substantially planar illumination beam 114 that subtends across, and is wider than, a lateral dimension of the fluid channel 104. The substantially planar illumination beam has an intensity profile that is wide in one direction orthogonal to the direction of travel of the beam (the width) while being narrow, relative to the wide direction, in another direction substantially orthogonal to both the direction of travel of the beam and the wide direction (the thickness). This substantially planar illumination beam is therefore a sheet-like illumination beam. The beam-shaping lens unit 112 can include, but is not limited to, a cylindrical lens. The detection system 110 includes an aperture stop 116 that defines a substantially rectangular aperture having a longitudinal dimension and a transverse dimension. The aperture stop 116 is arranged so that the rectangular aperture is confocal with an illuminated portion of the fluid channel such that the longitudinal dimension of the rectangular aperture substantially subtends the lateral dimension of the fluid channel without extending substantially beyond the fluid channel. In other words, the longitudinal, or long dimension, of the rectangular aperture is matched to, and aligned with, the illuminated width of the fluid channel 104. The transverse, or narrow dimension, of the rectangular aperture remains size matched to the narrow dimension, or thickness, of the illuminated sheet. Although the aperture is referred to as being substantially rectangular, it can be shapes other than precisely rectangular, such as an oval shape. In other words, the "substantially rectangular aperture" is longer in one dimension than in an orthogonal dimension. FIG. 9B shows the illumination light spread out to provide a substantially planar illumination beam 114. By arranging the substantially planar illumination beam 114 so that it extends sufficiently beyond the edges of the fluid channel 104 the bright central portion can be centered on the fluid channel. The aperture stop 116 can then be used to block light coming from regions outside of the desired illuminated slice of the fluid channel 104. The dimension of the beam expansion, the aperture size, and fluid channel size can be selected to achieve uniform detection across the channel according to an embodiment of the current invention. The beam is expanded such that the uniform center section of the Gaussian intensity profile covers the fluid channel. The remaining, non-uniform section is filtered out by the substantially rectangular aperture. For example, the substantially planar illumination beam incident upon said fluidic device is uniform in intensity across said fluid channel to within ±10% according to an embodiment of the current invention. To ensure that molecules within the microchannels are uniformly excited irrespective of position, the 1D beam expansion can be performed such that the max-min deviation across the microchannel is <20% according to some embodiments of the current invention. This leads to an optical measurement CV of ±6.5% due to illumination non-uniformity alone. For higher precision measurements, greater beam expansion can be performed at the cost of additional wasted illumination power. For example, given the same microchannel, a larger beam expansion can be performed such that the max-min variation is <5%, an optical measurement CV of <2% can be obtained.

In an embodiment of the current invention, we can use a 5 µm wide microchannel, for example. The aperture can be 600×50 µm (width×height). Given an 83-fold magnification, when the aperture is projected into sample space it ends up being about 7 µm wide, 2 µm wider than the channel. The laser beam is expanded to a $1/e^2$ diameter of about 35 µm, 7-fold wider than the channel width, where the excitation is most uniform. Thus, we only collect from the center 7 µm of the total 35 µm. Then, molecules flow through 5 µm of the available 7 µm (i.e., the microchannel). The narrow dimension of the aperture is size matched to the narrow, diffraction limited width the illumination line in the longitudinal direction to maximize signal to noise ratio. This provides approximately 100% mass detection efficiency with highly uniform beam intensity across the microchannel. However, the broad concepts of the current invention are not limited to this particular example.

The fluidic device 102 can be, but is not limited to, a microfluidic device in some embodiments. For example, the fluid channel 104 can have a width and/or depth than is less than a millimeter in some embodiments. The fluidic device can be, but is not limited to, a microfluidic chip in some embodiments. This can be useful for SMD using very small volumes of sample material, for example. However, other devices and structures that have a fluid channel that can be arranged proximate to the objective lens unit 106 are intended to be included within the definition of the fluidic device 102. For single fluorophore analysis, a fluid channel that has a width less than about 10 µm and a depth less than about 3 µm has been found to be suitable. For brighter molecule analysis, a fluid channel that has a width less than about 25 µm and a depth less than about 5 µm has been found to be suitable. For high uniformity analysis, a fluid channel has a width less than about 5 µm and a depth less than about 1 µm has been found to be suitable.

The objective lens unit 106 can be a single lens or a compound lens unit, for example. It can include refractive, diffractive and/or graded index lenses in some embodiments, for example.

The illumination system 108 can include a source of substantially monochromatic light 118 of a wavelength selected to interact in a detectable way with a sample when it flows through said substantially planar illumination beam in the fluid channel 104. For example, the source of substantially monochromatic light 118 can be a laser of a type selected according to the particular application. The wavelength of the laser may be selected to excite particular atoms and/or molecules to cause them to fluoresce. However, the invention is not limited to this particular example. The illumination system 108 is not limited to the single source of substantially monochromatic light 118. It can include two or more sources of light. For example, the illumination system 108 of the embodiment illustrated in FIG. 9A has a second source of substantially monochromatic light 120. This can be a second laser, for example. The second source of substantially monochromatic light 120 can provide illumination light at a second wavelength that is different from the wavelength from the first laser in some embodiments. Additional beam shaping, conditioning, redirecting and/or combining optical components can be included in the illumination system 108 in some embodiments of the current invention. FIG. 9A shows, schematically, an example of some additional optical components that can be included as part of the illumination system 108. However, the general concepts of the current invention are not limited to this example. For example, rather than free space combination f the illumination beam, the two or more beams of illumination light can be coupled into an optical fiber, such as a multimode optical fiber, according to an embodiment of the current invention.

The detection system 110 has a detector 122 adapted to detect light from said sample responsive to the substantially monochromatic light from the illumination system. For example, the detector 122 can include, but is not limited to, an avalanche photodiode. The detection system can also include optical filters, such as a band pass filter 124 that allows a selected band of light to pass through to the detector 122. The pass band of the band pass filter 124 can be centered on a wavelength corresponding to a fluorescent wavelength, for example, for the sample under observation. The detection system 110 is not limited to only one detector. It can include two or more detectors to simultaneously detect two or more different fluorescent wavelengths, for example. For example, detection system 110 has a second detector 126 with a corresponding second band pass filter 128. A dichroic mirror 130 splits off a portion of the light that includes the wavelength range to be detected by detector 126 while allowing light in the wavelength range to be detected by detector 122 to pass through. The detection system 110 can include various optical components to shape, condition and/or otherwise modify the light returned from the sample. FIG. 9A schematically illustrates some examples. However, the general concepts of the current invention are not limited to the particular example illustrated.

The cylindrical illumination confocal spectroscopy system 100 also has a dichroic mirror 132 that allows at least a portion of illumination light to pass through it while reflecting at least a portion of light to be detected.

The cylindrical illumination confocal spectroscopy system 100 can also include a monitoring system 134 according to some embodiments of the current invention. However, the monitoring system 134 is optional.

In addition, the detection system can also include a signal processing system 136 in communication with the detectors 122 and/or 126 or integrated as part of the detectors.

The cylindrical illumination confocal spectroscopy system 100 can be used to analyze single molecules, beads, particles, cells, droplets, etc. according to some embodiments of the current invention. The single molecules, beads, cells, particles, droplets, etc. can incorporate an entity such as a fluorophore, microparticle, nanoparticle, bead, etc. that elicits an optical signal that can be detected by the cylindrical illumination confocal spectroscopy system 100 according to some embodiments of the current invention. However, the general concepts of the current invention are not limited to these particular examples.

Examples

As depicted in FIG. 9A, high signal-to-noise detection can be enabled by the combination of a cylindrical lens (CL) 112 with a novel, microfabricated confocal aperture (CA) 116 according to an embodiment of the current invention. The cylindrical lens 112 is used to expand the illumination volume laterally in 1-D (along the x-direction or width) while remaining diffraction limited in the y-direction to maximize signal-to-noise ratio (FIG. 9B). Then, a confocal aperture is used to limit light collection to only the center section of the illumination volume (FIG. 9C). The microfabricated confocal aperture is neither round nor slit-like as in typical SMD but is rectangular and mimics the shape of the CICS observation volume. Whereas typical pinholes are nominally sized to the $1/e^2$ radius of the diffraction limited illumination volume (Centonze, V., and J. B. Pawley. 2006. Tutorial on Practical Confocal Microscopy and Use of the Confocal Test Specimen. In Handbook of Biological Confocal Microscopy. J. B. Pawley, editor. Springer, New York. 627-649), the CICS aperture is designed to occlude a much larger proportion of the illumination volume. Less than 30% of illumination volume in the x-direction is allowed to pass, such that a uniform, sheet-like observation volume is created. The final CICS observation volume is designed to be slightly larger than the accompanying microchannel in order to span the entire cross-section for uniform detection with near 100% mass detection efficiency, rectifying the limitations of traditional SMD without the drawbacks of molecular focusing or nanochannel confinement. This enables the resultant fluorescence bursts to not only be discrete but also to be so uniform they become digital in nature, ensuring accurate and robust quantification analysis.

CICS according to some embodiments of the current invention is shown to be superior to traditional SMD in accurate quantification and precise burst parameter determination. First, the limitations of traditional SMD and the potential benefits of CICS are theoretically explored using a combination of semi-geometric optics modeling and Monte Carlo simulations in the following examples. CICS is optimized for a 5×2 µm microchannel (w×h) and theoretically shown to have near 100% mass detection efficiency and <10% relative standard deviation (RSD) in the uniformity of detected fluorescence. Then, these models are validated using experimentally acquired observation volume profiles. Finally, CICS is implemented and demonstrated in two microfluidic systems through the detection of fluorescently stained DNA in a silicon device and a polydimethylsiloxane (PDMS) device and the detection of single Cy5 dye molecules in a PDMS device.

Materials and Methods

Numerical Simulation—Observation Volume

The observation volume (OV) profiles of confocal spectroscopy systems and their effects have been well explored in fluorescence correlation spectroscopy and SMD (Hess, S. T., and W. W. Webb. 2002. Focal volume optics and experimental artifacts in confocal fluorescence correlation spectroscopy. *Biophys. J.* 83:2300-2317; Enderlein, J., D. L. Robbins, W. P. Ambrose, and R. A. Keller. 1998. Molecular shot noise, burst size distribution, and single-molecule detection in fluid flow: Effects of multiple occupancy. *J. Phys. Chem. A* 102:6089-6094; Enderlein, J., D. L. Robbins, W. P. Ambrose, P. M. Goodwin, and R. A. Keller. 1997. Statistics of single-molecule detection. *J. Phys. Chem. B* 101:3626-3632; Goodwin, P. M., W. P. Ambrose, J. C. Martin, and R. A. Keller. 1995. Spatial dependence of the optical collection efficiency in flow-cytometry. *Cytometry* 21:133-144; Rigler, R., U. Mets, J. Widengren, and P. Kask. 1993. Fluorescence correlation spectroscopy with high count rate and low-background—analysis of translational diffusion. *Eur. Biophys. J. Biophy.* 22:169-175; Qian, H., and E. L. Elson. 1991. Analysis of confocal laser-microscope optics for 3-D fluorescence correlation spectroscopy. *Appl. Optics* 30:1185-1195; Chen, Y., J. D. Muller, P. T. So, and E. Gratton. 1999. The photon counting histogram in fluorescence fluctuation spectroscopy. *Biophys. J.* 77:553-567). We adopt a simple semi-geometric optics approach previously used by Qian and Rigler to theoretically model and guide the design of the CICS system (see Observation Volume Modeling below).

The code for simulation of the OV profiles was written in Matlab (The Mathworks, Cambridge, Mass.). In both simulations, the total observation volume, 10×10.2×12 μm (x×y×z), was discretized into 0.05×0.15×0.05 μm (x×y×z) elements. The OV function was evaluated at each element and stored in a 3D array for analysis. The image space, 8×8 μm, was discretized into 0.02×0.02 μm elements. The constants used for standard SMD simulation were: $w_o$=0.5 μm, $p_o$=75 μm, M=83.3, n=1.47, λ=525 nm, NA=1.35, and $r_o$=0.5 μm. The constants used for CICS simulation were: $x_o$=25 μm, $y_o$=0.5 μm, $z_o$=5 μm, $p_o$=300 μm, M=83.3, n=1.47, λ=525 nm, NA=1.35, and $r_o$=0.5 μm.

Observation Volume Modeling

The observation volume profile OV(r,z) reflects the detected intensity of fluorescence from a molecule located at a specific point (r,z). It can be calculated from the collection efficiency CEF(r,z) and illumination intensity I(r,z) using:

$$OV(r,z) = CEF(r,z) \times I(r,z) \quad (1)$$

where r=(x,y). The z axis is taken as the optical axis while the x axis and y axis run perpendicular and parallel to the direction of flow, respectively.

The illumination profile I(r,z) for traditional SMD can be approximated by that of a focused laser beam using a Gaussian-Lorentzian function:

$$I(r, z) = \frac{2P}{\pi w^2(z)} \exp\left(-2\frac{r^2}{w^2(z)}\right) \quad (2)$$

where P accounts for the illumination power of the laser. The beam waist radius w(z) can be found using:

$$w^2(z) = w_o^2 + z^2 \tan^2 \delta, \quad (3)$$

$$w_o = \frac{\lambda}{n\pi \tan \delta}, \quad (4)$$

where λ is the laser wavelength, n is the index of refraction, and E is the focusing angle of the laser beam at the 1/e² radius.

For CICS, since the illumination profile is expanded in 1-D and no longer radially symmetric, a 3-D Gaussian function is used:

$$I(r, z) = P \exp\left[-2\left(\frac{x^2}{x_0^2} + \frac{y^2}{y_0^2} + \frac{z^2}{z_0^2}\right)\right] \quad (5)$$

where $x_o$, $y_o$, and $z_o$ are the beam waist radii in the x, y, and z directions, respectively.

The collection efficiency CEF(r,z) represents the proportion of light collected by a point emitter located at (r,z). In confocal optics, the collection efficiency can be expressed as the convolution of the microscope point spread function PSF (r',r,z) and the confocal aperture transmission function T(r'):

$$CEF(r, z) = \frac{1}{\Delta} \int T(r') PSF(r', r, z) dr' \quad (6)$$

where r' is the image space coordinate and Δ is the normalization factor:

$$\Delta = \int circ\left(\frac{r'}{s_o}\right) PSF(r', 0, 0) dr'. \quad (7)$$

The microscope PSF reflects the image of a point source located at (r,z). As long as a highly corrected microscope objective is used, the microscope PSF can be assumed to be isoplanatic and isochromatic. It is approximated using:

$$PSF(r', r, z) = \frac{circ\left(\frac{r' - r}{R(z)}\right)}{\pi R^2(z)} \quad (8)$$

$$R^2(z) = R_o^2 + z^2 \tan^2 \alpha \quad (9)$$

where $R_o$ is the resolution limit of the objective and the numerical aperture is defined by NA=n sin α.

The aperture transmission function used is:

$$T(r) = circ\left(\frac{r}{s_0}\right) \quad (10)$$

$$circ\left(\frac{r}{s_0}\right) = \begin{cases} 1 & \text{if } |r| \leq s_o \\ 0 & \text{if } |r| > s_o \end{cases} \quad (11)$$

where $s_o$ is the pinhole radius in image space defined by $s_o = r_o/M$, $r_o$ is actual the pinhole radius, and M is the magnification at the pinhole. The same disk function is used for both traditional SMD and CICS simulations. The rectangular shape of the actual CICS aperture is not accounted for in the optical model. This leads to a slight overestimation of the background noise and underestimation of the signal variability.

Although using a semi-geometric optics model neglects higher order effects such as those resulting from diffraction and high-NA optics, the calculated OV profiles still provide a reasonable comparison between standard SMD and CICS as will be experimentally shown.

Numerical Simulation—Monte Carlo

Once the OV profiles are calculated, Monte Carlo simulations can be used to model the stochastic procession of molecules through the observation volume and the Poisson photoemission and detection process. This method is used to produce simulated single molecule trace data that can be analyzed in a manner identical to experimental data. During each time step, molecules are generated at random initial locations according to the concentration and propagated a distance in the y-direction according to the flow velocity.

The detected fluorescence intensity from a molecule at (r,z) can be calculated by:

$$I_f(r,z) = \beta_f OV(r,z) \Delta t \quad (12)$$

where $\Delta t$ is the integration time step and $\beta_f$ is a constant that accounts for factors such as the quantum yield and absorption coefficient of the fluorophore, the transmission of the optics, and the quantum efficiency of the detector.

The total collected fluorescence for all points within the observation volume can be found through integration over the entire volume:

$$I_f = \iiint \beta_f OV(r,z) dr dz \Delta t. \quad (13)$$

The same process can be repeated to calculate the background noise intensity $I_n$ by substituting the constant $\beta_n$ for $\beta_f$. The total collected intensity $I_t$ is given by:

$$I_t = I_f + I_n \quad (14)$$

The final signal, SMD, takes into account the Poisson photoemission and photodetection process:

$$SMD = Poi(Poi(I_t)) \quad (15)$$

Additional variability may be added to account for other sources of variability such as staining variability and variability in DNA length.

The Monte Carlo simulation was implemented in Matlab (The Mathworks, Cambridge, Mass.). Each fluorescent molecule has no volume and is assumed to be a point emitter. The models simulate 4 and 8 kb dsDNA stained at a 5:1 bp:dye ratio. The nominal DNA concentration was 1 pM unless otherwise indicated. A constant flow profile of v=1.5 mm/s was used in all simulations. Diffusion is ignored, and molecules travel in the y-direction only. A 0.1 ms time step was used, and all simulations were run for 100 s. Two data traces, one with and one without Poisson fluctuations in the photoemission and photodetection process, are stored, allowing accurate determination of mass detection efficiency. The signal-to-background ratio (SBR=average burst height/average background) was adjusted to match experimental data. In standard SMD, the simulation approximates the flow of molecules in a channel significantly larger than the observation volume. For CICS, a channel of 10.2×5×2 μm (l×w×h) was simulated.

CICS Instrumentation

All data were acquired with a custom-built, dual laser, dual detection channel, single molecule spectroscopy system capable of both traditional SMD and CICS with 488 nm and/or 633 nm laser illumination and detection at 520 nm and 670 nm. The beam from a 488 nm Ar-ion laser (Melles Griot, Carlsbad, Calif.) was expanded, collimated, and filtered using two doublet lenses (f=50 mm and f=200 mm, Thorlabs, Newton, N.J.) and a 150 μm pinhole (Melles Griot, Carlsbad, Calif.) arranged as a Keplerian beam expander. The beam from a 633 nm He—Ne laser (Melles Griot, Carlsbad, Calif.) is also expanded and filtered using similar optics. The two beams are spatially aligned using beam steering minors mounted on gimbals (U100-G2K, Newport, Irvine, Calif.) and combined using a dichroic minor (z633RDC, Chroma Technology, Rockingham, Vt.). The laser powers are individually adjusted using neutral density filters (Thorlabs, Newton, N.J.). In CICS mode, a cylindrical lens (f=300 mm, Thorlabs, Newton, N.J.) is used to shape the beam into a sheet and focused into the back focal plane of the microscope objective. The laser is then tightly focused by a 100× oil-immersion (1.4 NA) objective (100× UPlanFl, Olympus, Center Valley, Pa.). The fluorescence is collected by the same objective and spectrally separated from the excitation light using a second dichroic minor (z488/633RPC, Chroma Technology, Rockingham, Vt.). It is passed through a confocal aperture, further separated into two detection bands by a third dichroic mirror (XF2016, Omega Optical, Brattleboro, Vt.) and filtered by bandpass filters (520DF40 and 670DF40, Omega Optical, Brattleboro, Vt.) before being imaged onto silicon avalanche photodiodes (APD) (SPCM-CD2801 and SPCM-AQR13, PerkinElmer Optoelectronics, Fremont, Calif.) with f=30 mm doublet lenses (Thorlabs, Newton, N.J.). Holographic notch filters (HNPF-488.0-1 and HNPF-633.0-1, Kaiser Optical Systems, Ann Arbor, Mich.) are also used to reduce the background from scattered light. Using an f=150 mm doublet tube lens (Thorlabs, Newton, N.J.), the total magnification at the pinhole is ~83×. For standard SMD, a circular pinhole (Melles Griot, Carlsbad, Calif.) is used but for CICS, a rectangular, microfabricated confocal aperture is used. Data is collected from the APDs by a PC using a PCI6602 counter/DAQ card (National Instruments, Austin, Tex.) that is controlled using software written in Labview (National Instruments, Austin, Tex.). Samples are positioned using a combination of a computer controlled, high resolution piezoelectric flexure stage (P-517.3CL, PI, Auburn, Mass.) and a manual XYZ linear stage (M-462, Newport, Irvine, Calif.). The entire system was built on a pneumatically isolated optical table (RS2000, Newport, Irvine, Calif.).

Microfabricated Confocal Aperture

The confocal aperture is fabricated from a 4" silicon wafer (300 μm thick, (1,0,0), SSP, p-type). 60 μm thick SPR220-7 (Shipley) is patterned using a triple spin coat and used as a masking material for a through wafer inductively coupled plasma/reactive ion etch (Trion Phantom RIE/ICP). The etch simultaneously forms the rectangular aperture and releases the die as a 9.5 mm diameter disk that can be mounted into a XYZθ-stage (RSP-1T and M-UMR5.25, Newport, Irvine, Calif.) for alignment. Apertures of 620×115 μm and 630×170 μm were used. Since the alignment of the aperture is critical to the observation volume uniformity, a RetigaExi CCD (QImaging Corporation, Surrey, BC, Canada) is used to guide the alignment. Image analysis is performed using IPLab (BD Biosciences Bioimaging, Rockville, Md.)

Single Molecule Trace Data Analysis

Data analysis is performed using software written in Labview. A thresholding algorithm is first used to discern fluorescence bursts from background fluctuations. The threshold can be set either at a constant value or in proportion to the background fluctuation levels. The identified bursts can then be individually analyzed for burst width, burst height, and burst size after a background correction is performed. No smoothing algorithms are applied.

OV Profile Acquisition

OV profile analysis was performed on the 488-SMD and 488-CICS systems. The experimental OV profiles were acquired by scanning a 0.24 μm yellow-green CML fluorescent bead (Invitrogen, Carlsbad, Calif.) through the OV using a high resolution piezoelectric stage (PI, Auburn, Mass.) and recording the resultant fluorescence intensity as a function of position. A low excitation laser power of 0.008 mW/cm$^2$ was used to minimize photobleaching. The fluorescent beads were diluted to a concentration of 2×10⁶ beads/ml using DI water. A 5 µl drop of the diluted bead solution was placed onto a No. 1 thickness glass coverslip (Fisher Scientific) and allowed to dry. Then, the beads were covered with a thin layer of polydimethylsiloxane (PDMS, Dow Corning, Midland, Mich.) for protection (Cannell, M. B., A. McMorland, and C. Soeller. 2006. Practical Tips for Two-Photon Microscopy. In Handbook of Biological Confocal Microscopy. J. B. Pawley, editor. Springer, New York. 900-905). Beads were imaged from the backside through the glass. A rough 100×100 µm (x×y) scan was used to locate individual beads. Once an isolated bead was found, it was scanned in 0.15×0.15×0.15 µm (x×y×z) steps over a 4×4×8 µm volume for standard SMD and in 0.25×0.15×0.15 µm steps over a 12×6×10 µm volume for CICS. The fluorescence intensity was binned in 1 ms intervals and averaged over 25 ms at each point.

pBR322 DNA Preparation

For 488-SMD and 488-CICS analysis, pBR322 DNA (New England Biolabs, Ipswich, Mass., 4.3 kbp) was stained with PicoGreen (Invitrogen, Carlsbad, Calif.) using the protocol developed by Yan (Yan, X. M., W. K. Grace, T. M. Yoshida, R. C. Habbersett, N. Velappan, J. H. Jett, R. A. Keller, and B. L. Marrone. 1999. Characteristics of different nucleic acid staining dyes for DNA fragment sizing by flow cytometry. *Anal. Chem.* 71:5470-5480). The DNA was diluted to 100 ng/mL in TE buffer and stained with 1 µM PicoGreen for 1 hour in the dark. It was then further diluted down to 1 pM in TE buffer for measurement. For 633-SMD and 633-CICS analysis, pBR322 DNA was stained with TOTO-3 (Invitrogen, Carlsbad, Calif.). The DNA was diluted to 100 ng/mL in TE buffer and stained with TOTO-3 at a 5:1 base pair:dye ratio for 1 hour in the dark. It was then further diluted down to 1 pM in TE buffer for measurement.

Cy5 Oligonucleotide Preparation

Single Cy5 5' end-labeled 24 bp ssDNA (Integrated DNA Technologies, Coralville, Iowa, Cy5-5'-AAGGGATTC-CTGGGAAAACTGGAC-3') was resuspended in DI water and diluted to 1 pM concentration in filtered TE buffer for measurement.

633-SMD/Cy5 Analysis in a Microcapillary

A flow cell was fabricated using 100 µm ID fused silica microcapillary tubing (Polymicro Technology, Phoenix, Ariz.). A syringe pump (PHD2000, Harvard Apparatus, Holliston, Mass.) was used to drive the Cy5 labeled oligonucleotide through the flow cell at a volumetric flow rate of 1 µl/min. The input laser power was 0.185 mW/cm², and a 1 ms photon binning time was used. A typical trace consists of 300 s of data.

488-CICS pBR322/PicoGreen-DNA Analysis in Silicon Microfluidics

For 488-CICS analysis of pBR322 DNA, the cylindrical lens is inserted into the beam path, and the circular pinhole is swapped for a 620×115 µm rectangular confocal aperture. A microfluidic device was fabricated from silicon. First, 500× 5×2 µm (l×w×h) channels were etched into a 4", 500 µm thick, SSP, p-type, (1,0,0) silicon wafer using reactive ion etching and photoresist as a masking material. After etching, 0.8 mm through wafer fluidic vias were drilled into the silicon substrate using an abrasive diamond mandrel. Then, the channels were sealed by anodic bonding of 130 µm thick borosilicate glass (Precision Glass and Optics, Santa Ana, Calif.). Finally, Nanoport (Upchurch, Oak Harbor, Wash.) fluidic couplings were epoxied to the backside. A syringe pump was used to drive sample through the device at a typical volumetric flow rate of 0.001 µl/min such that the flow velocity was comparable to that of standard SMD. A 0.1 ms bin time was used. A typical trace consists of 300 s of data. The input laser power was 0.08 mW/cm².

633-CICS and 633-SMD/TOTO-3-DNA and Cy5 Oligonucleotide Analysis in PDMS Microfluidics For 633-CICS analysis of both TOTO-3 stained pBR322 DNA and Cy5, a 630×170 µm confocal aperture was used. Standard soft-lithography techniques (Younan Xia, G. M. W. 1998. Soft Lithography. *Angewandte Chemie International Edition* 37:550-575) were used to create 500×5×2 µm (l×w× h) PDMS channels bonded to #1 glass cover slips (Fisher Scientific, Pittsburg, Pa.). A syringe pump was used to drive sample through the device at a volumetric flow rate of 0.001 µl/min such that the flow velocity was comparable to that of standard SMD. A 0.1 ms bin time was used in the pBR322 DNA analysis while a 1 ms bin time was used in the Cy5 oligonucleotide analysis. A typical trace consists of 300 s of data. 1.85 mW/cm² and 0.057 mW/cm² illumination powers were used for CICS and SMD analysis of pBR322 DNA, respectively. 3.7 mW/cm² and 0.185 mW/cm² illumination powers were used for CICS and SMD analysis of Cy5 oligonucleotide, respectively.

Results

Observation Volume Modeling

Individual molecules that traverse the observation volume of CICS are detected uniformly irrespective of location or trajectory whereas fluorescent signals that are detected using traditional SMD are a strong function of molecular trajectory. It is this enhancement in observation volume uniformity that can enable CICS to be significantly more accurate, precise, and quantitative than traditional SMD. A semi-geometric optics model is used to theoretically compare the OV profiles of CICS with traditional SMD. FIGS. 10A-10F show the calculated illumination, collection efficiency, and OV profiles for standard SMD and CICS.

Figures 10A, 10B, 10C, 10D, 10E, 10F:
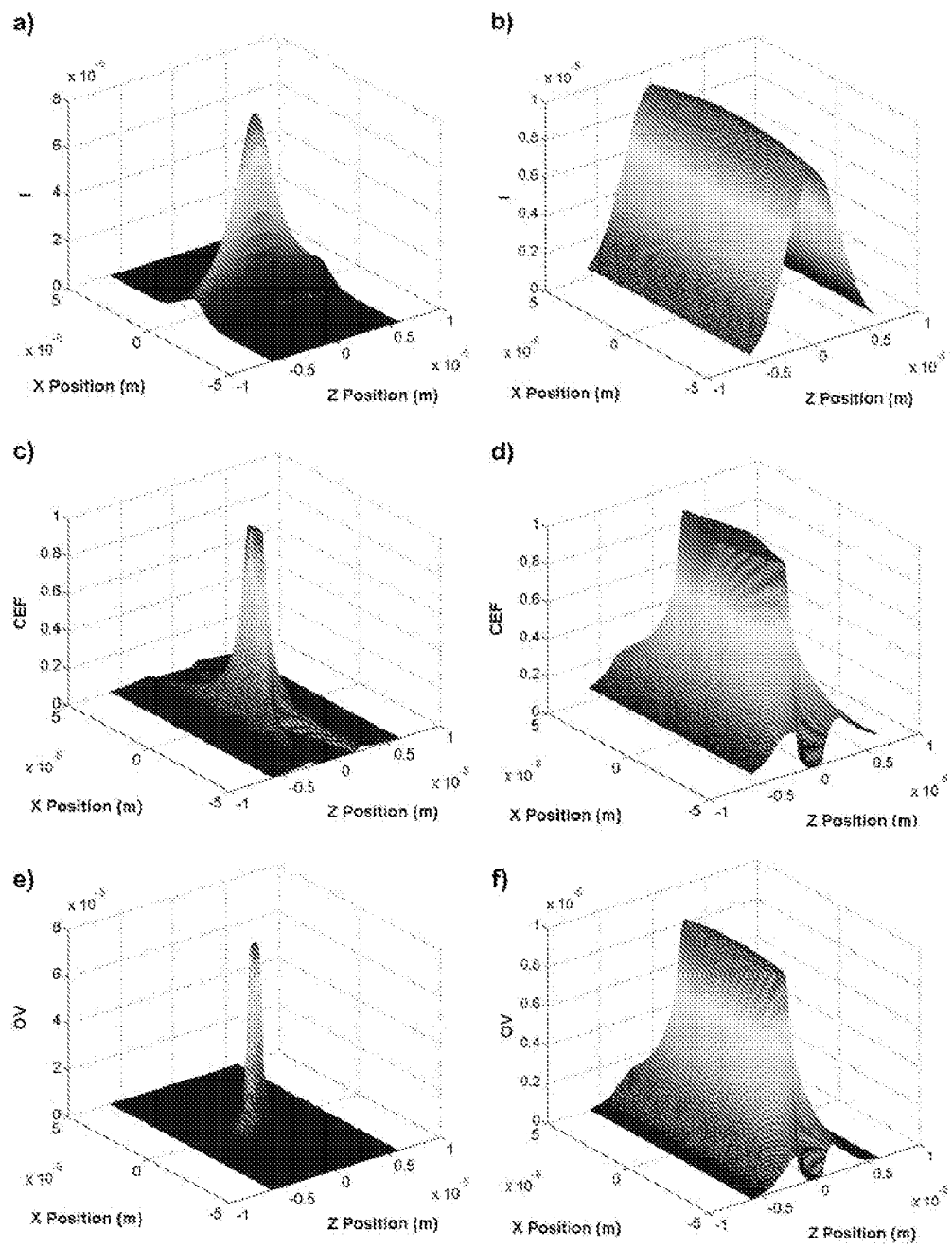

The increased uniformity of CICS is created by two key modifications to the standard confocal spectroscopy system. Standard SMD has a diffraction limited illumination profile that is radially symmetric and has a $1/e^2$ radius of approximately 0.5 µm (FIG. 10A). By using an appropriate cylindrical lens, this radius can be elongated in 1-D to approximately 25 µm to form a sheet of excitation light rather than a point (FIG. 10B). Since the illumination profile is expanded in 1-D perpendicular to flow only, noise from background is minimized while uniformity and mass detection efficiency are increased. Standard SMD also uses a small pinhole (~100 µm) such that the collection efficiency decays sharply at regions away from the confocal point (FIG. 10C). In CICS, a large pinhole or aperture (~600 µm) is used such that fluorescence can be uniformly collected from the entire 7×2 µm (w×h) center plateau region (FIG. 10D). However, with a standard pinhole the stray light is no longer optimally apertured due to the geometric discrepancy between the circular pinhole and the sheet-like illumination. For optimal results, a microfabricated rectangular aperture is used as subsequently described.

As shown in FIG. 10E, the result of the diffraction limited illumination profile and the sharply decaying collection efficiency is that traditional SMD has an OV profile that is nearly Gaussian in shape and varies sharply with position. Molecules that traverse the center of the observation volume result in much larger fluorescence bursts than molecules that travel through the edges, creating a train of highly variable single molecule bursts due to the typically random distribution of molecules in solution. This intrinsic variability makes accurate determination of burst parameters or burst frequency difficult. Conversely, due to the broad illumination profile and the uniform collection efficiency, FIG. 10F shows that the OV profile of CICS has a large plateau region of approximately 7×2 µm (w×h) where both excitation and detection occur in an extremely uniform manner. Over this plateau region, the detected fluorescence intensity is expected to have less than 10% RSD due to optical variation. Unlike standard SMD which requires nanochannel confinement (e.g. 0.35×0.25 µm, w×h) to achieve comparable performance (Foquet, M., J. Korlach, W. R. Zipfel, W. W. Webb, and H. G. Craighead. 2004. Focal volume confinement by submicrometer-sized fluidic channels. *Anal. Chem.* 76:1618-1626), CICS can be performed within a much larger microchannel (5×2 µm, w×h, >100× increase in cross-sectional area). Since the optimal microchannel is slightly smaller than the CICS observation volume, digital fluorescence bursts will be detected with near 100% mass detection efficiency.

Monte Carlo Simulations

To further explore the effects of the observation volume non-uniformity and molecular trajectory, the Monte Carlo method is used to generate simulated single molecule traces based on the theoretical OV profiles in FIGS. 10A-10F. Fluorescent molecules are generated at random initial locations and propagated through the observation volume according to the flow profile. During each time step, the fluorescence signal arising from all molecules within the observation volume as well as the background signal is integrated. FIGS. 11A and 11B, respectively, depict two simulated traces for a prototypical embodiment of traditional SMD performed within a channel that is larger than the observation volume and CICS performed within a 5×2 µm (w×h) microchannel. As expected, traditional SMD shows a smaller number of highly variable bursts due to the non-uniform OV profile while CICS shows a larger number of highly uniform bursts that appear digital due to the smooth plateau region.

The burst rate of CICS increases in direct proportion to the 1-D expansion. The large enhancement in mass detection efficiency is achieved through the combination of this increase in burst rate due to the observation volume expansion and the use of a microchannel that is size matched to the observation volume. The mass detection efficiency can be accurately analyzed in the simulation through a comparison of all randomly generated molecules against those detected after thresholding. When a discrimination threshold of 30 counts is applied, the mass detection efficiency of CICS within the 5×2 µm channel (w×h) is 100% with no false positives or false negatives due to the digital nature of the fluorescence bursts. If the channel size is further increased to 7×3 µm (w×h), the mass detection efficiency remains at 100% but the burst height variability increases from 13% RSD to 26% RSD, illustrating the tradeoff between observation volume size, throughput, and detection uniformity (data not shown).

In fact, the variability in burst height is no longer dominated by non-uniformity in the OV profile but rather the Poisson photoemission and detection process. Although the uniformity can be improved by changing the collimation optics and aperture should a larger observation volume be necessary, there will be a concurrent decrease in signal-to-noise ratio that is unavoidable. Further improvements must be found by increasing the fluorescence intensity through higher illumination powers or from longer photon binning times instead of optical modifications.

In contrast, since traditional SMD is usually performed within a channel that is much larger than the observation volume, it has an extremely low mass detection efficiency. For example, given a 100 µm ID microcapillary, the mass detection efficiency is less than 0.05% under the same threshold. This low mass detection efficiency is due to a combination of the minute observation volume, observation volume non-uniformity, thresholding artifacts, and Poisson fluctuations. The large majority of molecules (>99.6%) escape detection because of the size mismatch between the observation volume and the microcapillary. The remainder of the molecules (~0.3%) is missed since their corresponding fluorescence bursts reside below the threshold and are indistinguishable from background fluctuations. To obtain 100% mass detection efficiency using standard SMD, nanochannel confinement or molecular focusing of molecules to a stream width of <<1 µm would be necessary.

Detailed analysis of the Monte Carlo data reveals that when thresholding algorithms are used to discriminate fluorescence bursts from background fluctuations, as is common practice, the quantification accuracy of traditional SMD is compromised due to thresholding artifacts. The burst rate is defined as the rate at which fluorescence bursts are detected and is proportional to the concentration of molecules in the sample as well as the sample flow rate and mass detection efficiency. The burst height is then defined as the maximum number of photon counts per bin time emitted by a molecule during a transit event. It is related to the brightness of the molecule, the observation volume uniformity, the flow rate, and photon binning time. The wide distribution of burst heights in standard SMD causes the burst rate and determined burst parameters to vary widely with the specific threshold applied as shown in Table 3. As the threshold is increased, the smaller bursts are progressively excluded, gradually decreasing the burst rate and shifting the average burst height upwards. Accurate determination of the absolute burst rate and burst height is extremely difficult since it is nearly impossible to distinguish between small fluorescence bursts arising from molecules that traverse the periphery of the observation volume and random background fluctuations. In contrast, since CICS bursts are uniform in size, they are much more robust when used with thresholding algorithms. The applied threshold can vary over a wide range without affecting either the burst rate or determined burst parameters. This is due to the digital nature of the fluorescence bursts. The average burst height determined using CICS remains extremely constant as the threshold is varied from 20 to 70 counts, increasing only 4% whereas the average burst height determined using traditional SMD increases 100%.

TABLE 3

Thresholding artifacts in traditional SMD versus CICS

| | Traditional SMD | | CICS | |
|---|---|---|---|---|
| Threshold (counts) | Burst Rate/ 100s | Burst Height (counts) | Burst Rate/ 100s | Burst Height (counts) |
| 20 | 421 | 149 ± 199 | 958 | 101 ± 24 |
| 30 | 305 | 197 ± 216 | 906 | 105 ± 14 |
| 40 | 257 | 227 ± 223 | 906 | 105 ± 14 |
| 50 | 224 | 254 ± 226 | 906 | 105 ± 14 |
| 60 | 206 | 272 ± 229 | 906 | 105 ± 14 |
| 70 | 183 | 298 ± 229 | 903 | 105 ± 14 |

Analysis of 100s Monte Carlo simulation data. The digital nature of fluorescence bursts acquired using CICS allows the system to be robust against thresholding artifacts. However, quantitative burst parameters determined using traditional SMD are highly sensitive to the specific threshold applied. The bin time was 0.1 ms.

Matters are further complicated when molecules of varying brightness need to be quantified using the burst rate. Two populations of molecules of equal concentration but different brightness levels can give significantly different burst rates even if the same threshold is applied, necessitating precise calibration for each molecular species. These effects are illustrated in Table 4. The simulated DNA is stoichiometrically stained such that the number of incorporated dye molecules and, hence, brightness increases linearly with DNA length. Although the total quantity of DNA is conserved in all cases, the burst rate of standard SMD can vary by almost 40% when presented with only a 2× increase in DNA length. With standard SMD, it is impossible to determine concentration based on burst rate alone. Prior knowledge of the sample composition is necessary to provide an accurate reference standard. When an unknown mixture of molecules of varying brightness is present, such calibrations are often infeasible as it becomes impossible to independently separate the effects of brightness and concentration. CICS, however, is highly robust even when quantifying mixtures of molecules as shown in Table 4. A constant quantity of DNA is reflected even in the presence of varying mixtures. The burst rates differ by less than 5% in the same situation, implicating that concentration can be blindly determined based on burst rate alone.

TABLE 4

Single molecule burst rates in varying DNA mixtures

|  | 1 pM 4 kbp | 1 pM 8 kbp | 0.5 pM 4 kbp + 0.5 pM 8 kbp | 0.25 pM 4 kbp + 0.75 pM 8 kbp |
|---|---|---|---|---|
| Traditional SMD | 305 | 420 | 381 | 410 |
| CICS | 915 | 928 | 948 | 922 |

Simulated burst rate of DNA mixtures taken using traditional SMD and CICS. The burst rate of traditional SMD varies as relative proportions of the two DNA components are varied although the total concentration is conserved in all cases. The CICS burst rate remains consistent across the mixtures. The applied threshold was 30 counts, and the bin time was 0.1 ms.

These Monte Carlo simulations have theoretically shown that the 1-D expansion of the observation volume and increase in observation volume uniformity provide the basis for CICS to achieve 100% mass detection efficiency within a microchannel and to perform highly accurate and robust burst parameter analysis. CICS rectifies the limitations of traditional SMD while still preserving single molecule sensitivity.

Experimental Observation Volume Mapping

The OV profiles of the 488-SMD and the 488-CICS systems were acquired by rastering a sub-micron fluorescent bead through the observation volume and recording the collected fluorescence intensity as a function of position. FIGS. 12A and 12B, show xz-plots that track the theoretical predictions of FIGS. 10A-10F. Standard SMD has a small, sharply decaying OV profile that can be accurately modeled using a 3-D Gaussian approximation. Excellent fits to Gaussian functions were obtained resulting in measured $1/e^2$ radii of 0.33, 0.44, and 0.99 μm in the x, y, and z directions, respectively; this leads to an observation volume size of 0.6 fL (see FIGS. 13A, 13C and 13E). However, the observation volume is not perfectly symmetrical and contains some aberrations. These are likely due to artifacts caused by optical aberrations, misalignment of optical components, mechanical drift and instability of the scanning stage, and photobleaching of the fluorescent bead.

The CICS system, on the other hand, shows a much larger, elongated observation volume that is fairly uniform in the center section. The OV profile of CICS mirrors that of traditional SMD in the y-($y_0$=0.25 μm) and z-directions ($z_0$=1.18 μm) but is elongated in the x direction ($x_{uniform}$~7 μm) as designed (see FIG. 13). This is further illustrated in FIGS. 13B-13D where a CCD is used to take images of the standard SMD and CICS illumination volumes using a reflective interface held perpendicular to the optical axis. In FIG. 13B, the $1/e^2$ radius of the illumination volume in the x-direction (width) is stretched to 12.1 μm using an f=300 mm cylindrical lens (see FIG. 14). n FIG. 13C, a 620×115 μm confocal aperture limits light collection to only the center 7 μm where the illumination is most uniform (see FIG. 15). Over this region there is roughly a 6% RSD and 15% maximum variation in illumination intensity. Since the characteristic dimensions of the observation volume are larger than the 5×2 μm (w×h) microchannel used to transport molecules, near 100% mass detection efficiency is expected as theoretically predicted (Stavis, S. M., J. B. Edel, K. T. Samiee, and H. G. Craighead. 2005. Single molecule studies of quantum dot conjugates in a submicrometer fluidic channel. *Lab on a chip* 5:337-343). For analysis using 633-CICS, the confocal aperture was increased to 630×170 μm (w×h) to increase signal intensity and reduce the axial dependence of collection uniformity.

Despite the general agreement, the experimental CICS OV profile lacks the distinct plateau present in the theoretical simulations. This is expected as the sharp plateau is a limitation of the semi-geometric optics approximation used. In practice, the sharp cutoff in collection efficiency defined by the aperture is replaced by a smooth decay. In addition, the dependence of the OV profile in the z-dimension is much sharper than that predicted by the model. This can possibly be rectified through the use of a lower N.A. microscope objective or larger confocal aperture. Finally, there is additional non-uniformity introduced by diffraction, optical aberrations, mis-alignment, and experimental error that are not accounted for in the theoretical simulations. Similar point spread functions have recently been reported in confocal line scanning applications (Ralf, W., Z. Bernhard, and K. Michael. 2006. High-speed confocal fluorescence imaging with a novel line scanning microscope. *J. Biomed. Opt.* 11:064011; Dusch, E., T. Dorval, N. Vincent, M. Wachsmuth, and A. Genovesio. 2007. Three-dimensional point spread function model for line-scanning confocal microscope with high-aperture objective. *J. Microsc.* 228:132-138). Together, these effects increase the non-uniformity over theoretical predictions. Further improvements in uniformity can still be had through the incorporation of an objective with a higher degree of aberration correction, improved optical alignment, increased mechanical stability, and minor refinements in optical design.

DNA Analysis

For the preliminary demonstration of CICS, analysis was performed on bright, multiply stained pBR322 DNA molecules. Initially, a silicon based microfluidic chip containing 5×2 μm microchannels was used to precisely transport molecules through the uniform 7×2 μm CICS observation volume. 488-CICS was first used to analyze PicoGreen stained pBR322 DNA. The experimental trace (see FIG. 16) is characterized by a large number of uniform fluorescence bursts and shows strong similarities to the simulated trace of FIG. 11B. It has a high burst rate of 1955 bursts/300 s when a detection threshold of 22 counts is applied and average burst height of 33.0±10.4 counts (RSD=31%). However, accompanying the large increase in burst rate and uniformity is a substantial increase in background. The large increase in background is greater than that expected from the observation volume expansion alone. The close proximity of the glass-water interface at the top of the channel and the opaque silicon at the bottom of the 2 μm high microchannel creates large amounts of scattered light, significantly increasing background levels and leading to a low SBR of 6 (SBR=average burst height/average background). This scatter background is more effectively rejected by the smaller pinhole in standard SMD than the larger, rectangular aperture in CICS. In order to prevent the background from swamping out the fluorescent bursts, the illumination power was limited to only 0.08 mW/cm$^2$. Therefore, in the subsequent experiments a transition to a glass-PDMS device was made.

In order to compare CICS with SMD, a second microfluidic device of identical geometry to the first was fabricated out of PDMS and glass using soft-lithography. The transparent PDMS-glass materials have lower scatter background than the opaque silicon previously used. Red excitation (633 nm) with far red detection (670 nm) was found to have a lower average background and fewer spurious fluorescent bursts when used with PDMS devices than blue excitation (488 nm) with green detection (520 nm). It is believed that this can be attributed to the PDMS autofluorescence (Cesaro-Tadic, S., G. Dernick, D. Juncker, G. Buurman, H. Kropshofer, B. Michel, C. Fattinger, and E. Delamarche. 2004. High-sensitivity miniaturized immunoassays for tumor necrosis factor alpha using microfluidic systems. *Lab on a chip* 4:563-569; Piruska, A., I. Nikcevic, S. H. Lee, C. Ahn, W. R. Heineman, P. A. Limbach, and C. J. Seliskar. 2005. The autofluorescence of plastic materials and chips measured under laser irradiation. *Lab on a chip* 5:1348-1354; Yokokawa, R., S. Tamaoki, T. Sakamoto, A. Murakami, and S. Sugiyama. 2007. Transcriptome analysis device based on liquid phase detection by fluorescently labeled nucleic acid probes. *Biomedical microdevices* 9:869-875) as well as the large number of organic contaminants and impurities that fluoresce in green. As a result, TOTO-3 stained pBR322 DNA was analyzed rather than the previous PicoGreen stained DNA. The low scatter background enabled 633-CICS to be run at 1.85 mW/cm$^2$ rather than the low 0.08 mW/cm$^2$ previously used in 488-CICS. To achieve comparable illumination power densities at the observation region, 633-SMD was operated at 0.059 mW/cm$^2$ to account for the greater than 30× decrease in illumination volume size (see FIGS. 17 and 18). FIG. 25 shows two single molecule traces taken using 633-SMD (top) and 633-CICS (bottom). These traces closely resemble the Monte Carlo data in FIG. 11. The CICS traces show a higher burst rate, more uniform fluorescent bursts, and a slightly higher background than the SMD traces. Standard SMD, at a discrimination threshold of 10 counts, shows 336 bursts in a 300 s period with an average burst height of 51.5±44.6 counts (RSD=87%). It is difficult, though, to set a threshold where both false negative and false positive bursts are minimized. Setting the threshold at the standard μ+3 σ level, which gives a 99.7% confidence interval, would lead to an average of 9000 false positive peaks when acquiring data over a 300 s period with a 0.1 ms bin time. Thus, it is necessary to use a significantly higher threshold at the cost of an increased number of false negatives. Since there is no optimal threshold setting, it is difficult to determine the accuracy of the absolute burst rate and burst parameters.

CICS burst data, on the other hand, is much less sensitive to thresholding artifacts as predicted by the model. Using a threshold of 100 counts, 1278 fluorescent bursts were detected over a 300 s period where the average burst height was 211.6±56.6 counts (RSD=27%). When the threshold is varied over a wide range of 65-135 counts, the number of detected bursts decreases only 11% whereas in standard SMD the burst rate decreases by 44% over a much smaller range of 6-14 counts (see FIG. 19). The price to pay for the increased uniformity and burst rate is a correlated reduction in SBR. While the 633-CICS SBR of 22 is much improved over the previous 488-CICS results performed within the silicon devices due to the decreased scattering background in the PDMS devices, it is still less than SBR of 271 obtained using 633-SMD. This reduction in SBR using CICS is fairly consistent but slightly more than that expected from the ~7× linear expansion in observation volume size.

Since the channel dimensions of the silicon and PDMS devices are identical, the burst height uniformities are expected to be similar as is seen. However, they are approximately 10% greater than that which was theoretically predicted. Further uniformity improvements can be expected if the axial dependence (z-direction) is reduced through lower N.A. collection optics such as a 1.2 N.A. water immersion objective. The remainder of variability can be attributed to factors such as variability staining efficiency, fluctuations in the illumination intensity, instabilities in the flow velocity, and the Poiseuille flow profile.

Two significant drawbacks of the PDMS devices that were not encountered using the silicon devices were frequent flow instabilities and long transient times when changing flow velocities. This can likely be attributed to the elastic nature of the PDMS and the less robust nature of the fluidic couplings. These effects become apparent as short time scale fluctuations in the burst rate (~seconds), longer time scale drift (~tens of minutes), and sudden spikes in burst rate. They are exacerbated by the intrinsic difficulty in controlling such low flow rates (0.001 μl/min) as well as the high flow resistance of the small microchannels. From the optical characterizations and simulations, it is evident that the 7×2 μm observation volume is sufficient to span the entire 5×2 μm microchannel. While based on the uniformity of the burst height histogram (see FIG. 20), it is evident that nearly all the molecules are flowing through the uniform center section of the observation volume. This implies that the large majority of molecules within the channel are in fact being detected. Thus, we believe the decreased burst rate can be largely attributed to flow variability.

Although the observation volume here was expanded ~7×, which corresponded to a roughly 10× decrease in SBR from standard SMD, it can be tailored to almost any size using the correct combination of cylindrical lens and aperture. The required signal-to-noise ratio and observation volume uniformity will dictate the maximum focal volume expansion that can be performed while maintaining adequate sensitivity.

Single Fluorophore Sensitivity

CICS was tested to see if single fluorophore sensitivity was preserved despite the observation volume expansion. Cy5 labeled 24 bp ssDNA was diluted to 1 pM, flowed through the PDMS microfluidic device, and analyzed using both traditional SMD and CICS. CICS was run at 3.7 mW/cm$^2$ while SMD was performed at 0.185 mW/cm$^2$. A longer photon binning time (1 ms vs. 0.1 ms) was used in the single fluorophore Cy5 experiments to increase signal levels. When standard SMD is performed within a large capillary, Cy5 fluorophores can be detected with a SBR of 13 and 89% RSD in burst height (threshold=8 counts, average burst height=18.0±16.1 counts). Whereas when standard SMD is performed within the microchannel, the scatter background is increased due to the close proximity of the glass-water and water-PDMS interfaces resulting in a slightly reduced SBR of 10 (see FIG. 21) while burst height RSD remains at a comparable 90% (average burst height=36.7±32.9 counts) when a threshold of 14 is applied. In comparison, CICS is significantly more uniform (see FIG. 21). The average Cy5 burst height was 120.8±58.9 counts, which corresponds to a RSD of 49% (threshold=254 counts). This burst uniformity is expected to be decreased when compared to the pBR burst uniformity because of the decreased brightness of the single Cy5 fluorophore. CICS showed an SBR of 1.6 which was 6× lower than the standard SMD SBR, consistent with the 7× increase in observation volume size. This illustrates the trade-off in uniformity, burst rate, and SBR that can be easily predicted and engineered using CICS. For single fluorophore analysis, the current 7×2 µm OV/5×2 µm microchannel combination is likely the largest expansion that can be performed while retaining single fluorophore sensitivity. But for brighter molecules such as fluorescent beads, quantum dots, or multiply labeled DNA or proteins, it is expected that even larger microchannels may be used for increased throughput.

Single Fluorophore Mass Detection Efficiency

As previously discussed, single Cy5 fluorophores are readily detected by both standard SMD and CICS. The estimation of mass detection efficiency requires an accurate determination of the absolute burst rate, which is in turn highly influenced by the specific threshold applied. The optimal threshold balances the proportion of false positive bursts against the proportion of false negative bursts in the attempt to minimize the influence of both. However, when analyzing dim molecules such as single fluorophores where the fluorescent fluctuations are not fully resolved from the background fluctuations (i.e. the distribution of fluorescent fluctuations overlaps the distribution of background fluctuations), this becomes extremely difficult since every threshold chosen will introduce an inordinate number of either false positives or false negatives. We adapt the method of Huang et al. to extrapolate the true burst rate from that determined after thresholding (Huang, B., H. K. Wu, D. Bhaya, A. Grossman, S. Granier, B. K. Kobilka, and R. N. Zare. 2007. Counting low-copy number proteins in a single cell. *Science* 315:81-84). Given the applied flow rate (0.001 µl/min) and nominal concentration (1 pM), an average of ~3011 molecules are expected to flow through the channel during each 300 s period. Using standard SMD, 232 molecules can be detected leading to a mass detection efficiency of 7.5% (see FIG. 22). This burst rate appears somewhat lower than expected. Under CICS analysis, on the other hand, 3467 molecules can be detected (see FIG. 23). Although this number is slightly greater than the expected number of molecules, this difference may be attributed to errors in flow rate due to pump calibration, instabilities in flow as previously discussed, pipetting errors in sample preparation, and inaccuracies in the data analysis method.

The large mass detection efficiency increase in CICS is achieved through the combination of two effects, a decrease in the size of the transport channel and a matched 1-D increase in observation volume size. Standard SMD mass detection efficiencies (<1%) are low since the transport channel (diameter ~100 µm) is typically much larger than the SMD observation volume (diameter ~1 µm). Since the mass detection efficiency describes the relative proportion of detected molecules, a reduction in transport channel size increases mass detection efficiency without a concurrent increase in burst rate while an increase in observation volume size increases both mass detection efficiency and burst rate. As the channel size is reduced to below the observation volume size, the mass detection efficiency is maximized while the absolute burst rate is progressively reduced. Using the previous method, standard SMD performed in a 100 µm diameter capillary achieves a mass detection efficiency of only 0.04% (see FIG. 24). By substituting a 5×2 µm microchannel, the mass detection efficiency is increased to 7.5% while the absolute burst rate is actually reduced by 5× since the low microchannel height limits the effective size of the observation volume. This 7.5% roughly correlates to the overlap in cross-sectional area between the SMD observation volume size and the microchannel, but is slightly lower than the 10-15% expected, likely due to flow instabilities, a slight misalignment of the channel to the observation volume, and inaccuracy in the estimation method. To increase mass detection efficiency to near 100% using standard SMD, a nanochannel must be used (Stavis, S. M., J. B. Edel, K. T. Samiee, and H. G. Craighead. 2005. Single molecule studies of quantum dot conjugates in a submicrometer fluidic channel. *Lab on a chip* 5:337-343). However, CICS further increases mass detection efficiency by matching the 5×2 µm microchannel with an optimized 1-D observation volume expansion. This leads to a 15× increase in absolute burst rate over standard SMD in a microchannel and near 100% mass detection efficiency. The observation volume in CICS can be easily tailored to span a given channel geometry with the correct choice of optics and aperture using the methods previous described.

Burst Size Distribution Analysis (BSDA)

Not only is CICS more accurate in quantification and burst parameter determination, the greatly enhanced uniformity enables single molecule assays that cannot be performed using traditional SMD. For example, burst size distribution analysis uses the distribution of individual fluorescence burst intensities to determine the size of a molecule. As shown in FIG. 26, the Gaussian OV profile of standard SMD does not allow a clear distinction of the pBR DNA population from the background fluctuations. However, the same DNA shows a clear population centered around 151 counts when analyzed using CICS. Thus, the average burst size can be more accurately determined without being skewed by background fluctuations. In fact, the digital fluorescence bursts even obviate the need for smoothing algorithms such as Lee filtering when processing such data (Enderlein, J., D. L. Robbins, W. P. Ambrose, P. M. Goodwin, and R. A. Keller. 1997. The statistics of single molecule detection: An overview. *Bioimaging* 5:88-98). Using CICS, it is possible to perform a burst size distribution assay on a mixture of DNA molecules and individually identify the constituents of that mixture as well as their individual concentrations. Such an assay would be impossible using standard SMD.

Through careful modeling and implementation, CICS has been engineered to alleviate the subtle shortcomings of traditional SMD that make it difficult to apply in a widespread manner. CICS significantly enhances uniformity and mass detection efficiency while still preserving single fluorophore sensitivity, allowing more accurate and precise determination of single molecule parameters than traditional SMD. It can be operated with higher throughput and with less complication than competing technologies using molecular focusing and molecular confinement. In addition, its quantification accuracy is further reinforced by its robustness against thresholding artifacts. Finally, because CICS uses an epi-fluorescent arrangement, it is easily used with essentially all types of microfluidic devices including those with opaque substrates such as silicon. This makes it an ideal detection platform that can be generically combined with all microfluidic systems. Since the mass detection efficiency, detection uniformity, and signal-to-noise ratio can be accurately predicted, it can be easily optimized for any microfluidic channel size and application. CICS has great potential in applications such as clinical diagnostics, biochemical analysis, and biosensing where accurate quantification of the molecular properties of rare biomolecules is necessary.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above (including U.S. provisional application 61/111,064, filed Nov. 4, 2008, and U.S. application Ser. No. 12/612,300, filed Nov. 4, 2009) and in the figures, are hereby incorporated in their entirety by reference.

We claim:

1. A method for determining the size distribution of cell-free DNA molecules in a sample, comprising
    labeling the cell-free DNA molecules in the sample with a fluorescent dye in a stoichiometric manner,
    subjecting the labeled DNA to single molecule spectroscopy, and
    measuring fluorescent burst parameters and fluorescent burst rate of the labeled DNA,
    wherein the fluorescent burst parameters, which comprise burst size, burst height and/or transit time, indicate the length of each of the DNA molecules; and the fluorescent burst rate indicates the abundance of each size of DNA molecule, and
    conducting single molecule DNA integrity analysis (smDIA) of the labeled DNA molecules in the sample, thereby determining the size distribution of the cell-free DNA molecules.

2. The method of claim 1, wherein the single molecule spectroscopy in carried out using flow cytometry.

3. The method of claim 1, wherein the single molecule spectroscopy is carried out using nanochannels.

4. The method of claim 1, wherein the single molecule spectroscopy is cylindrical illumination confocal spectroscopy (CICS).

5. The method of claim 1, wherein the single molecule spectroscopy is microfluidic cylindrical illumination confocal spectroscopy (μCICS).

6. The method of claim 1, wherein the single molecule spectroscopy is conducted by
    causing the sample comprising the labeled DNA molecules to flow through a channel of a fluidic device,
    illuminating a portion of the fluid flowing through the channel substantially uniformly with a sheet-like beam of light that activates the fluorescent dye,
    directing fluorescing light from the labeled DNA molecules to be detected through a substantially rectangular aperture of an aperture stop to be detected,
    wherein the substantially rectangular aperture is constructed and arranged to substantially match a width of said channel, and
    detecting the labeled DNA molecules based on light directed through the substantially rectangular aperture.

7. The method of claim 1, wherein the smDIA comprises
    correlating substantially quantized light pulses with the lengths of the DNA molecules detected, and
    calculating the single molecule DNA integrity (smDI, the ratio of long bursts to short bursts) of DNA molecules in the sample.

8. The method of claim 7, wherein the distinction between long and short DNA bursts is defined by a predetermined cut-off value or range of values.

9. The method of claim 7, further comprising comparing the smDI to a positive and/or a negative reference standard.

10. The method of claim 1, wherein the sample is a body fluid.

11. The method of claim 1, which is a method for determining if a subject is likely to have a cancer, wherein
    the sample is a body fluid from the subject,
    the single molecule spectroscopy is CICS or μCICS, and
    the smDIA comprises correlating substantially quantized light pulses with the lengths of the DNA molecules detected, and calculating the single molecule DNA integrity (smDI) of DNA molecules in the sample,
    wherein the smDI is compared to a predetermined cut-off value, and
    wherein an smDI of at least about 0.04, 0.06, 0.08, 0.10, 0.125, 0.15, 0.175, 0.2, 0.3, 0.4, 0.5, 0.6, 0.7, 0.8, or 0.9 indicates that the subject is likely to have the cancer.

12. The method of claim 1, which is a method for determining the tumor load in a subject compared to one or more reference standards, wherein
    the sample is a body fluid from the subject,
    the single molecule spectroscopy is CICS or μCICS, and
    the single molecule DNA integrity analysis (smDIA) comprises correlating substantially quantized light pulses with the lengths of the DNA molecules detected, and calculating the single molecule DNA integrity (smDI) of DNA molecules in the sample,
    further comprising
    comparing the smDI of the DNA molecules in the sample to a positive and/or a negative reference standard,
    wherein the negative and positive reference standards are representative of defined amounts of tumor load.

13. The method of claim 12, which is a method to determine if a subject is likely to have a cancer,
    wherein the negative reference standard is representative of the tumor load in a subject that does not have the cancer; and the positive reference standard is representative of the tumor load in a subject that has the cancer,
    wherein an smDI of the DNA molecules in the sample that is statistically significantly greater than the negative reference standard, and/or is approximately the same as the positive reference standard, indicates that the subject is likely to have the cancer.

14. The method of claim 13, which is a method for detecting a cancer at stage 1 or stage 2.

15. The method of claim 12, which is a method to stage a cancer in the subject,
    wherein the negative reference standard is representative of the tumor load in a subject that does not have the cancer, or has an early stage cancer, and the positive reference standard is representative of the tumor load in a subject that has a late stage cancer,
    wherein an smDI that is approximately the same as the negative standard indicates that the subject is likely to have an early stage cancer, and an smDI that is statistically significantly greater than the negative reference standard, or is approximately the same as the positive standard, indicates that the subject is likely to have a more advanced stage of the cancer.

16. The method of claim 12, which is a method to determine if a tumor is benign or malignant,
    wherein the negative reference standard is representative of the tumor load in a subject that has a benign tumor, and the positive reference standard is representative of tumor load in a subject that has a malignant cancer,
    wherein an smDI that is approximately the same as the negative standard indicates that the subject is likely to have a benign tumor, and an smDI that is statistically significantly greater than the negative reference standard, or is approximately the same as the positive standard, indicates that the subject is likely to have a malignant tumor.

17. The method of claim 12, which is a method for monitoring the progress or prognosis of a cancer in a subject, comprising determining the smDI at various times during the course of the cancer,
wherein a decrease in the smDI over the course of the analysis indicates that cancer is going into remission and that the prognosis is likely to be good, and an increase in the smDI over the course of the analysis indicates that cancer is progressing and that the prognosis is not likely to be good.

18. The method of claim 12, which is a method for evaluating the efficacy of a cancer treatment, comprising measuring the smDI at different times during the treatment,
wherein a change in the smDI over the course of the analysis indicates whether the cancer treatment is efficacious.

19. The method of claim 1, wherein the fluorescent dye is an intercalating dye, is covalently bound to the DNA through a coupling reaction, is introduced into the DNA though an enzymatic reaction, or is incorporated into the DNA by the binding of a labeled fluorescent probe.

20. The method of claim 1, wherein the fluorescent dye is TOTO-3.

21. The method of claim 1, wherein the method is high throughput.

22. The method of claim 1, wherein the subject is human.

23. The method of claim 1, wherein DNA in the sample is not separated from other components in the sample.

24. The method of claim 1, further comprising introducing a fluorescent tracer particle during single molecule spectroscopy to control for flow velocity, focus position and/or fluorescent intensity.

25. The method of claim 11, wherein the cancer is ovarian, breast, lung, prostate, colorectal, esophageal, pancreatic, prostate, head and neck, gastrointestinal, bladder, kidney, liver, lung, or brain cancer, gynecological, urological or brain cancer, or a leukemia, lymphoma, myeloma or melanoma.

26. The method of claim 11, wherein the sample is generated from a pleural effusion, ascites sample, plasma, serum, whole blood, urine, ductal lavage or sputum.

27. A method for determining the size distribution of DNA molecules in a sample, comprising
labeling the DNA molecules in the sample with a fluorescent dye in a stoichiometric manner,
subjecting the labeled DNA to single molecule cylindrical illumination confocal spectroscopy (CICS), such that a uniform detection profile is produced, and
measuring fluorescent burst parameters and fluorescent burst rate of the labeled DNA,
wherein the fluorescent burst parameters, which comprise burst size, burst height and/or transit time, indicate the length of each of the DNA molecules; and the fluorescent burst rate indicates the abundance of each size of DNA molecule, and
conducting single molecule DNA integrity analysis (smDIA) of the labeled DNA molecules in the sample, thereby determining the size distribution of the DNA molecules.

28. The method of claim 27, wherein the CICS is conducted in a cylindrical illumination confocal spectroscopy system as described in Example III.

* * * * *